US012677811B2

(12) United States Patent
Xu et al.

(10) Patent No.: US 12,677,811 B2
(45) Date of Patent: Jul. 14, 2026

(54) METHOD FOR CONSTRUCTING MURINE MODEL WITH MUTATIONS IN CSFLR GENE AND APPLICATION THEREOF

(71) Applicants:Beijing Tiantan Hospital, Capital Medical University, Beijing (CN); Yangzhou University, Yangzhou (CN)

(72) Inventors: Jun Xu, Beijing (CN); Xiaohong Wang, Yangzhou (CN); Yanli Wang, Beijing (CN); Jiwei Jiang, Beijing (CN); Linlin Wang, Beijing (CN); Shiyi Yang, Beijing (CN)

(73) Assignee: Beijing Tiantan Hospital, Capital Medical University, Beijing (CN)

( * ) Notice: Subject to any disclaimer, the term of this patent is extended or adjusted under 35 U.S.C. 154(b) by 399 days.

(21) Appl. No.: 18/545,693

(22) Filed: Dec. 19, 2023

(65) Prior Publication Data

US 2024/0206441 A1 Jun. 27, 2024

(30) Foreign Application Priority Data

Dec. 23, 2022 (CN) .......................... 202211663356.4

(51) Int. Cl.
| | |
|---|---|
| *A01K 67/0276* | (2024.01) |
| *A61K 49/00* | (2006.01) |
| *C07K 14/715* | (2006.01) |
| *C12N 15/85* | (2006.01) |

(52) U.S. Cl.
CPC ...... *A01K 67/0276* (2013.01); *A61K 49/0008* (2013.01); *C07K 14/7153* (2013.01); *C12N 15/8509* (2013.01); *A01K 2217/054* (2013.01); *A01K 2227/105* (2013.01); *A01K 2267/0356* (2013.01); *C12N 2015/8527* (2013.01)

(58) Field of Classification Search
CPC .......... A01K 67/0276; A01K 2217/054; A01K 2227/105; A01K 67/0275; A61K 49/0008; C07K 14/7153; C07K 14/705; C07K 14/723; C07K 14/53; C12N 15/8509; C12N 2015/8527; C12N 9/12; C12Y 207/10001
See application file for complete search history.

(56) References Cited

U.S. PATENT DOCUMENTS 11,396,549 B2 7/2022 Chen et al.

FOREIGN PATENT DOCUMENTS

| | | | | |
|---|---|---|---|---|
| CN | 112522321 A | | 3/2021 | |
| CN | 113046390 A | * | 6/2021 | ......... C12N 15/8509 |
| CN | 113811331 A | | 12/2021 | |
| CN | 113930446 A | | 1/2022 | |
| CN | 113981071 A | | 1/2022 | |
| WO | WO-2019133752 A1 | | 7/2019 | |

OTHER PUBLICATIONS

First Examination Report and Search Report of CNIPA.
Notice of Allowance from CNIPA and Allowed Claims.

* cited by examiner

*Primary Examiner* — Jeremy C Flinders
*Assistant Examiner* — Masudur Rahman

(57) ABSTRACT

A mutated Csf1r gene is disclosed. The mutated Csf1r gene is obtained by changing the 2557th nucleotide of a Csf1r gene from C to A, leading to obtain a mutated protein encoded by the mutated Csf1r gene substitute the 853rd amino acid from proline to threonine. The mutated protein, expression vectors, recombinant viruses, recombinant cells, recombinant bacteria, or recombinant vectors are also disclosed. A method for constructing a murine model with mutations in Csf1r gene. This method includes introducing the targeted vector containing the mutated Csf1r gene into mouse embryonic stem cells, followed by injection into blastocysts to generate F0 generation mice. The F0 generation mice are then bred with mice that specifically express Cre enzyme in tissues, followed by screening. The constructed murine model has significant applications in studying the pathogenic mechanisms of brain diseases caused by microglial cell dysfunction and screening valuable medicine for treating brain diseases.

6 Claims, 13 Drawing Sheets

Specification includes a Sequence Listing.

Wildtype allele

Targeting vector

5'arm (9.75 kb; EcoRV)

3'arm (10.90 kb; NsiI)

C57/BL6                              Csflr^P853T/+

C57/BL6                              Csflr^P853T/+

C57/BL6

Csflr P853T/+

C57/BL6

Csflr P853T/+

Spleen

Brainstem

METHOD FOR CONSTRUCTING MURINE MODEL WITH MUTATIONS IN CSFLR GENE AND APPLICATION THEREOF

CROSS REFERENCE OF RELATED APPLICATIONS

The present application claims priority of Chinse Patent Application No. 202211663356.4, filed on Dec. 23, 2022, entitled "Method for Constructing Murine Model with Mutations in Csf1r Gene, and Application thereof," in the China National Intellectual Property Administration (CNIPA), the entire contents of which are hereby incorporated by reference in their entireties.

REFERENCE TO AN ELECTRONIC SEQUENCE LUSTING

The contents of the electronic sequence listing (11-SE-Q.xml; Size: 37,825 bytes; and Date of Creation: Dec. 20, 2023) is herein incorporated by reference in its entirety.

FIELD OF THE DISCLOSURE

The disclosure relates to the field of animal model construction techniques, and especially to a method for constructing a murine model with mutations in Csf1r (Colony Stimulating Factor 1 Receptor) gene, and applications thereof.

BACKGROUND OF THE DISCLOSURE

Functional impairment of microglia resulting from mutations in the Csf1r gene is a rare leukodystrophy. Clinically, it often manifests as rapidly progressive cognitive dysfunction, parkinsonian-like motor impairment, and psychiatric behavioral abnormalities. Imaging reveals conspicuous alterations in brain white matter, ventricular enlargement, brain atrophy, dysgenesis of the corpus callosum, multiple scattered calcifications and so on. Pathological anatomy findings include characteristic axonal spheroid accompanied by pigmented glial, diffuse axonal degeneration and demyelination. The disease was formerly known by various names such as hereditary diffuse leukoencephalopathy with spheroids (HDLS), adult-onset leukodystrophy with neuroaxonal spheroids and pigmented glia (ALSP), and Csf1r-related encephalopathy, all based on these distinctive phenotypic features.

In the human genome, the Csf1r gene is located on the q32 region of the long arm of chromosome 5, and in mice the Csf1r gene is located on chromosome 18. The Gene ID of the Csf1r is 12978 in NCBI. The Csf1r protein is a receptor protein primarily distributed on the cell surface, comprising five functional domains. The five functional domains include 5 immunoglobulin-like motifs in the extracellular domain, a transmembrane domain, a juxtamembrane domain, and two tyrosine kinase domains. As of September 2022, a total of 126 pathogenic mutation sites have been reported worldwide, with approximately 90% located within the two tyrosine kinase domains. In vitro studies have identified two possible mechanisms by which Csf1r mutations lead to impaired autophosphorylation function: one involving a negative regulatory mechanism, mutations within the juxtamembrane domain or the kinase insert region result in reduced kinase activity, inhibiting downstream target phosphorylation; the other involving a loss-of-function mechanism, mutations within the tyrosine kinase domains lead to kinase inactivation, rendering it incapable of further signal transduction. However, the mechanisms in vivo remain unclear. Previously, a missense mutation c.2563C>A (p.P855T) in exon 20 of the Csf1r gene was initially identified in a family with hereditary diffuse leukoencephalopathy with spheroids (HDLS). Through validation within the family and research involving conditional knockout mouse models, it has been confirmed that the c.2563C>A point mutation in the Csf1r gene is a pathogenic site causing brain diseases associated with microglial dysfunction.

SUMMARY OF THE DISCLOSURE

The first object of the present invention is to provide a mutated Csf1r gene, mutated protein, expression cassette, recombinant virus, recombinant cell, recombinant bacterium, or recombinant vector.

The second object of the present invention is to provide a method for constructing a murine model with mutations in the Csf1r gene.

The third object of the present invention is to provide an application of the method for constructing a mutated Csf1r gene and a murine model with Csf1r gene mutation in the preparation of medicine for the treatment of brain diseases caused by microglial dysfunction.

The present invention provides a mutated Csf1r gene, where the 2557th nucleotide of the Csf1r gene has mutated from C to A, as shown in SEQ ID NO: 1.

The present invention further provides a mutated Csf1r protein encoded by the aforementioned mutated gene. The mutated Csf1r protein features a substitution of proline with threonine at the 853rd amino acid position of the Csf1r protein. The amino acid sequence of the mutated Csf1r protein is shown in SEQ ID NO: 2.

The present invention further provides expression cassettes, recombinant viruses, recombinant cells, recombinant bacteria, or recombinant vectors containing the mutated Csf1r gene.

The present invention further provides a method for constructing a murine model with mutations in the Csf1r gene, comprising the following steps:

(1) constructing a targeting vector, $Csf1r^{P853T/+}$, containing the mutated Csf1r gene;

(2) electroporating the targeting vector $Csf1r^{P853T/+}$ obtained in step (1) into mouse embryonic stem cells and verifying positive clones.

(3) injecting the verified positive mouse embryonic stem cells from step (2) into blastocysts and transplanting the blastocysts into the uteri of female mice to obtain F0 generation mice.

(4) breeding the F0 generation mice obtained in step (3) with mice that express Cre enzyme in a tissue-specific manner and selecting F1 generation heterozygous mice that carry both the point mutation described in step (1) and the Cre gene in their genomes.

(5) pairing any two heterozygous F1 generation mice obtained in step (4) and selecting F2 generation homozygous mice, thereby obtaining the desired murine model.

Preferably, the mice that express Cre enzyme in a tissue-specific manner are mice that express Cre enzyme in macrophages.

Preferably, the F2 generation homozygous mice are mice afflicted with brain diseases caused by microglial dysfunction.

The present invention further provides an application of any of the mutated Csf1r gene, mutated Csf1r protein, expression cassette, recombinant virus, recombinant cell, recombinant bacterium, or recombinant vector, and the construction method in the preparation of medicine for the treatment of brain diseases caused by microglial dysfunction.

Advantages: Compared to the prior art, the present invention offers the following significant benefits: (1) In contrast to other genetically modified or knockout mouse models of microglial encephalopathy, the present invention can simulate a broader range of psychiatric symptoms in addition to cognitive impairments, including the manifestation of both manic and depressive symptoms, as well as schizophrenia-like symptoms. (2) The present invention can replicate peripheral symptoms of clinical microglial encephalopathy, such as skeletal developmental anomalies, splenic structural damage and hyperfunction, systemic inflammation, ascites, colonic ulcerative inflammation, and other symptoms. (3) The present invention allows for the observation of the characteristic pathological structure of microglial encephalopathy—axonal spheroids. (4) These mice have a longer lifespan, making it convenient for longitudinal observation of changes in behavior, pathology, and gene expression levels at different levels. (5) There are significant differences in pathology and behavior between female and male mice.

DETAILED DESCRIPTION OF THE DISCLOSURE

The following description is provided in conjunction with the accompanying figures to further elucidate the technical approach of the present invention.

Example 1: Construction of a Murine Model with Csf1r Gene Mutations

Step 1, Constructing the Vector

Figure 1A:
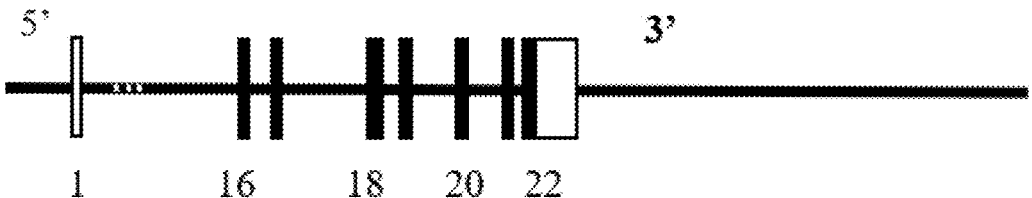
FIG. 1A is a schematic diagram showing the wild-type Csf1r gene.

As shown in FIG. 1A, the Csf1r gene sequence, shown in SEQ ID NO: 3, is located on mouse chromosome 18 and comprises 22 exons. The start codon ATG is situated in exon 2, while the stop codon TGA is located in exon 22. The amino acid sequence encoded by the Csf1r gene is shown in SEQ ID NO: 4. The mutation site involves the change of the 2557th nucleotide of the Csf1r gene from C to A, resulting in the mutated Csf1r gene shown in SEQ ID NO: 1. The mutation also leads to the substitution of proline with threonine at the 853rd amino acid position of the Csf1r protein, giving rise to the mutated Csf1r protein with the amino acid sequence shown in SEQ ID NO: 2.

The mutation introduced at the 853rd amino acid position encoded by the Csf1r gene corresponds to the 2557th nucleotide position in the cDNA. Primers were designed to introduce the P853T (CCC to ACC) mutation into exon 20.

Figure 1B:
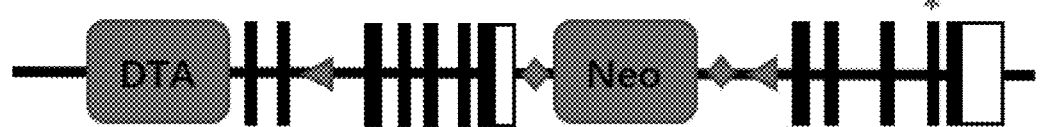
FIG. 1B is a schematic diagram showing the linear vector for constructing Csf1r$^{P853T/+}$, where the triangle symbols indicate LoxP sites, the diamond symbols indicate SDA (self-deletion anchor) sites, and the asterisk symbols represent the point mutation sites.

The construction of the vector, as shown in FIG. 1B, involves the Csf1r$^{P853T/+}$ targeting vector, which is a linearized vector containing the P853T (CCC to ACC) mutation site. The vector also includes common elements such as DTA, loxP, sdNeo cassette, SDA, and others. The sequence of the Csf1r$^{P853T/+}$ targeting vector is shown in SEQ ID NO: 5. This vector was constructed by Saiye (Guangzhou) Biotechnology Co., Ltd.

Step 2, Electroporation

C57BL/6N ES cells were resuscitated and passaged using serum-free mouse embryonic stem cell culture medium (OriCell, MUXES-90061, Saiye (Guangzhou) Biotechnology Co., Ltd.). Approximately 1×10$^7$ cells were counted and resuspended in electroporation buffer. To this cell suspension, 35 μg of the linearized Csf1r$^{P853T/+}$ targeting vector obtained in Step 1 was added and thoroughly mixed. The mixture was then allowed to sit on ice for 5 minutes. The cell suspension was transferred to an electroporation cup, and electroporation was performed using the following param- eters: 250V, 500 μF, and a single pulse. After electropora- tion, the cells were transferred to culture dishes pre-seeded with G418-resistant MEF cells. Subsequent culture was carried out using serum-containing mouse embryonic stem cell culture medium (OriCell, MUXES-90011, Saiye (Guangzhou) Biotechnology Co., Ltd.).

After 24 hours, selection was initiated by adding G418 (final concentration 200 μg/mL) to the serum-containing mouse embryonic stem cell complete medium (OriCell, MUXES-90061, Saiye (Guangzhou) Biotechnology Co., Ltd.). Over a period of 7 days, daily observation and medium changes were performed. Following the completion of drug selection, surviving clones were picked and trans- ferred to a 96-well plate for further passaging and culture.

Figure 2:
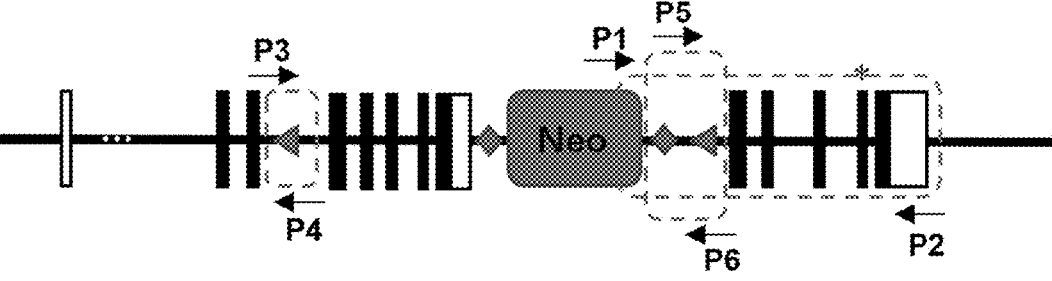
FIG. 2 is a schematic diagram showing the PCR primer design sites.

Step 3, PCR Screening:

PCR amplification and electrophoresis were used to screen the clones obtained in Step 2. The primer design sites are shown in FIG. 2, and their specific sequences are provided in the table below:

Neo-F1:
AAGGCGATAGAAGGCGATGC;

Neo-R1:
TCATCTCACCTTGCTCCTGC.

Figure 7:
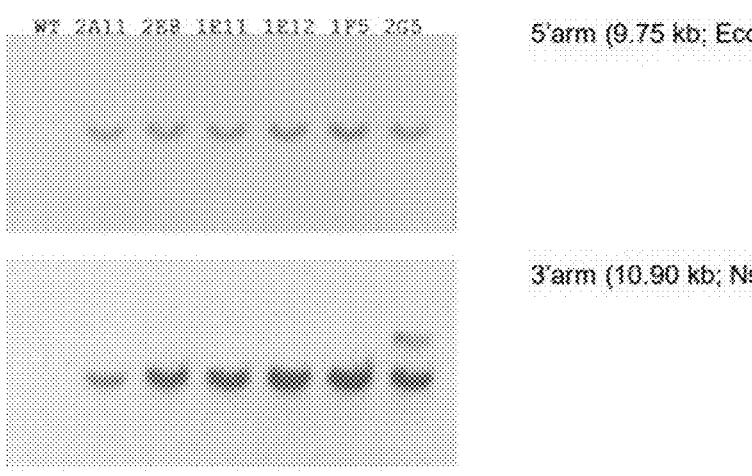
FIG. 7 shows the results of Southern blot detection.

In Southern analysis, the Neo probe can detect the fol- lowing DNA fragments from the target allele: ~9.75 kb (digested with EcoRV) and ~10.90 kb (digested with NsiI). Among the six ES clones, five (2A11, 2E8, 1E11, 1E12, and 1F5) were confirmed as positive through Southern blot detection, as shown in FIG. 7.

Step 5, Mouse Breeding

ES cells were injected into embryos, and the embryos were then transplanted into the uteri of surrogate mother mice. The surrogate mother mice gave birth to the F0 generation of genetically engineered mice, known as Knock- out-floxed mice. After reaching 8 weeks of age, the Knock- out-floxed mice were housed together with 8-week-old mice that expressed Cre enzyme specifically in macrophages (Saiye (Suzhou) Biotechnology Co., Ltd.). This breeding resulted in the F1 generation of heterozygous Csf1r$^{P853T/+}$ mice. A pair of F1 generation mice were selected for mating to obtain the F2 generation of homozygous Csf1r$^{P853T/+}$

TABLE 1

Primer Design

| Region | | Sequence | The anticipated length of the PCR product | |
| --- | --- | --- | --- | --- |
| | | | Wildtype allele | Targeting allele |
| 3'arm | Neo-F1 (P1) | 5'-GGCTGGTAAGGGATA TTTGCCTG-3' | N.A. | ~4.6 kb |
| | 3'arm-R (P2) | 5'-TCATGCTCCAAGAAA TTGTGGTAGA-3' | | |
| loxP site | loxP-F (P3) | 5'-GCTGCTTCTCCTCATA AAACATAGT-3' | 219 bp | 259 bp |
| | loxP-R (P4) | 5'-ATTTGCATACACAAC AACCCGTTAG-3' | | |
| Neo site | Neo-F2 (P5) | 5'-CTTGGCTGGACGTAA ACTCCTC-3' | N.A. | 273 bp |
| | Neo-R (P6) | 5'-AAGTACACAATACCA GGTGCTTTC-3' | | |

Figure 3:
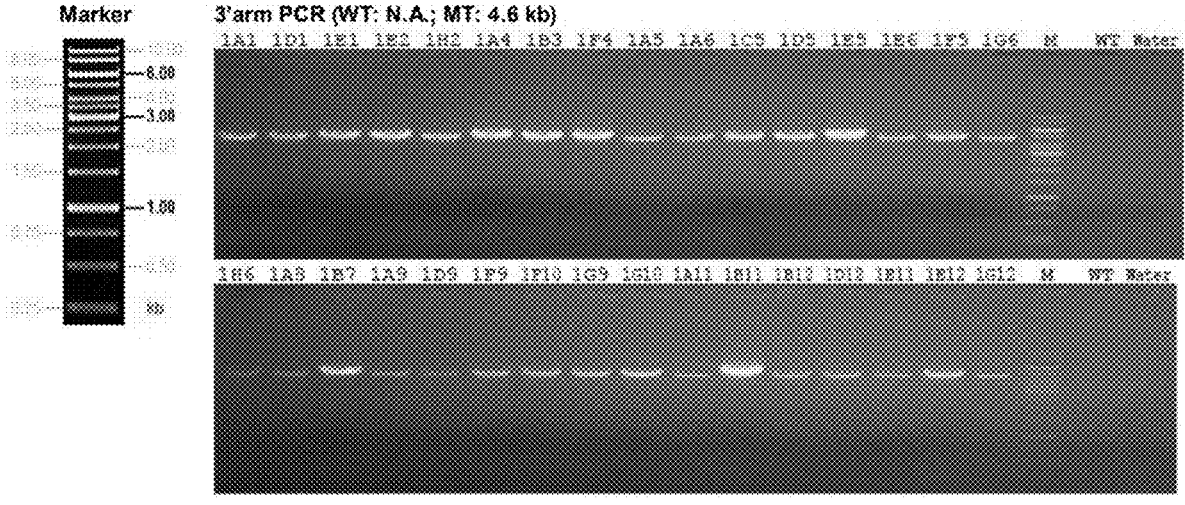
FIG. 3 shows the results of positive clone PCR screening at the 3' arm end.
Figure 3:
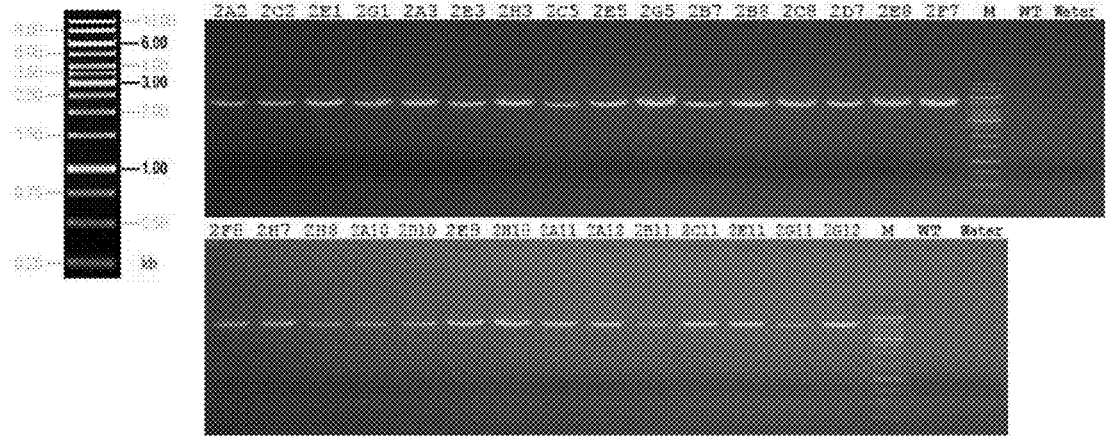
Figure 4:
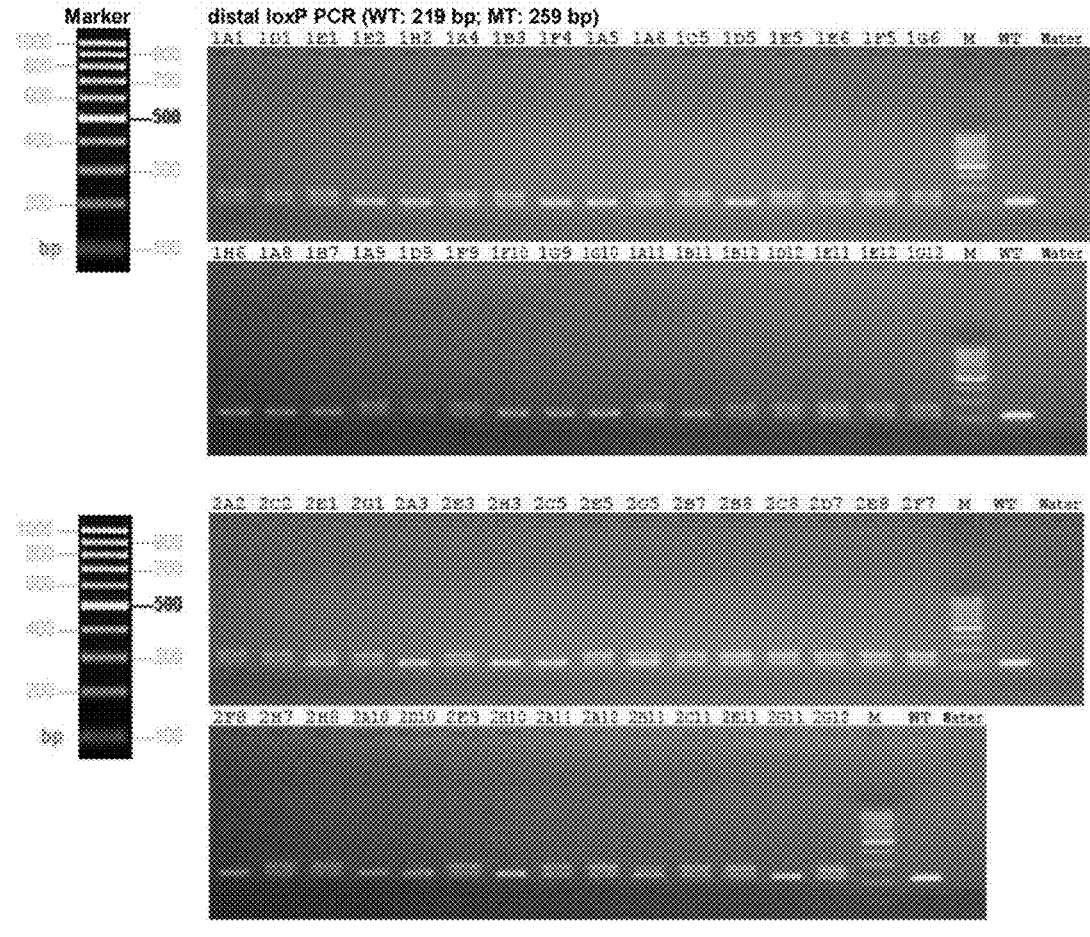
FIG. 4 shows the results of positive clone PCR screening at the far-end LoxP site.
Figure 5:
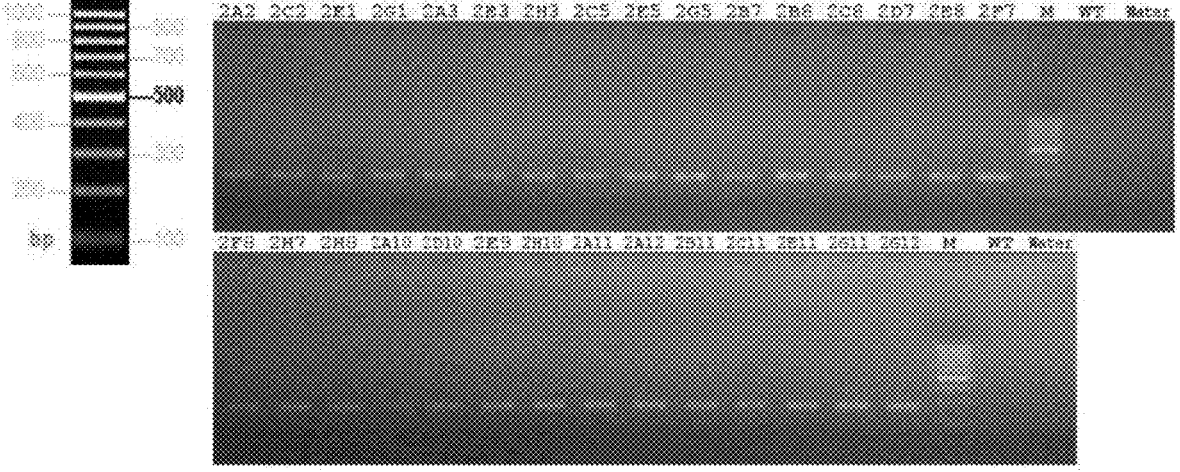
FIG. 5 shows the results of positive clone PCR screening at the Neo site.
Figure 5:
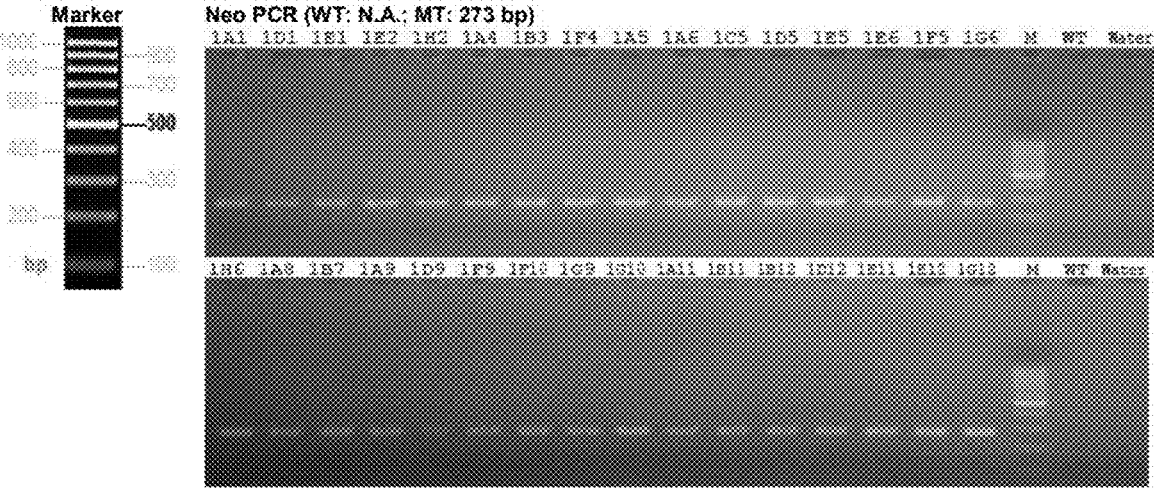

The results of the 3'arm end positive clone PCR screening are shown in FIG. 3, the results of the far-end loxP site positive clone PCR screening are shown in FIG. 4, and the results of the Neo site positive clone PCR screening are shown in FIG. 5. Samples 1A1, 1D1, 1E1, 1A4, 1B3, 1A6, 1C5, 1E5, 1E6, 1F5, 1G6, 1A9, 1D9, 1F9, 1A11, 1B12, 1D12, 1E11, 1E12, 1G12, 2A2, 2C2, 2E1, 2G1, 2E3, 2E5, 2G5, 2B7, 2B8, 2C8, 2D7, 2E8, 2F7, 2H7, 2H8, 2E9, 2A1, 2A12, 2B11, 2C11, 2E11, and 2G12 are sequenced. Among these samples, 1C5, 1F5, 1A9, 1E11, 1E12, 2C2, 2E3, 2G5, 2E8, 2H7, 2A11, 2A12, 2C11, and 2E11 were confirmed as potential target ES clones through sequencing.

Step 4, Southern Blot for Positive ES Cell Selection

Figure 6:
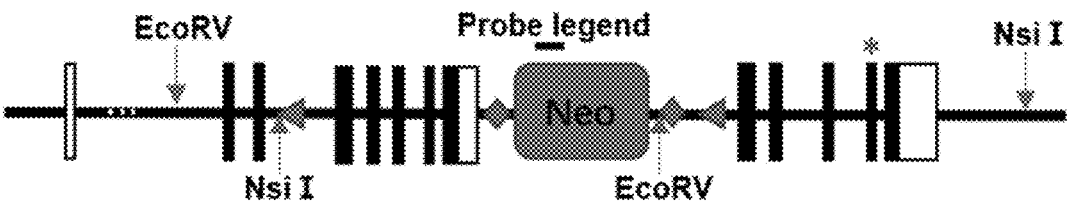
FIG. 6 shows the design of the Southern blot detection region.
Figure 8:
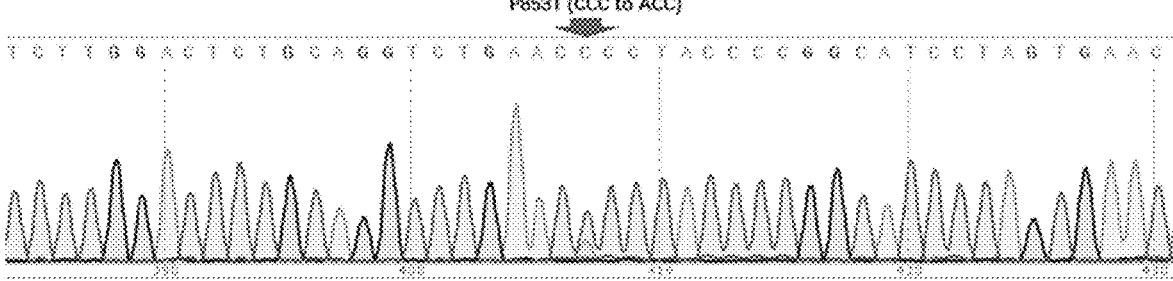
FIG. 8 shows the sequencing results of the Csf1r gene point mutation, changing from CCC to ACC.

Positive clones (2A11, 2E8, 1E11, 1E12, 1F5, and 2G5) identified through PCR screening were further amplified and subjected to Southern blot analysis for confirmation. The Southern blot detection region is outlined in FIG. 6. Genomic DNA was digested using either EcoRV or NsiI, and hybridized with a Neo probe. The sequences of the Neo probe primers are as follows:

mice. Sequencing was performed to confirm the presence of the single-base mutation at the 2557th nucleotide position of the Csf1r gene cDNA, as shown in FIG. 8. This mutation corresponds to the designed mutation site, confirming the successful generation of F2 generation homozygous Csf1r$^{P853T/+}$ mice with macrophage-specific expression of the mutated Csf1r gene.

Example 2: Cognitive Assessment of Csf1r$^{P853T/+}$ Mice

Experimental Materials: Csf1r$^{P853T/+}$ mice constructed in Example 1, aged 8 months, weighing between 25-28 g, ad libitum feeding; C57/BL6 wild-type mice (sourced from the Comparative Medicine Center at Yangzhou University), aged 8 months, weighing between 25-28 g, ad libitum feeding.

Figure 9A:
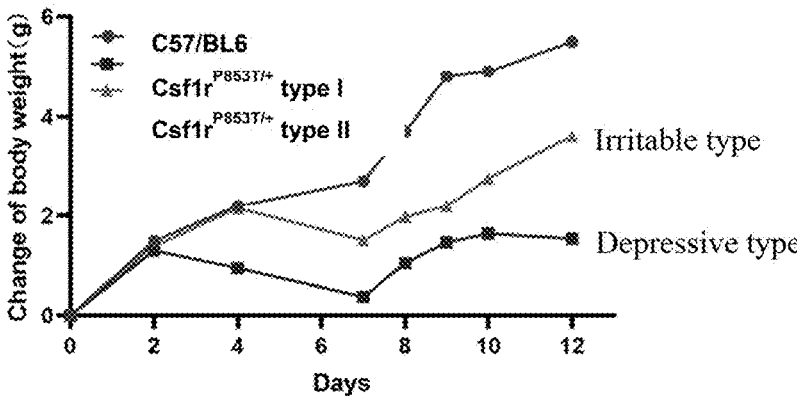
FIG. 9A shows the weight gain graph for C57/BL6, Csf1r$^{P853T/+}$ type I, and Csf1r$^{P853T/+}$ type II mice.
Figure 9B:
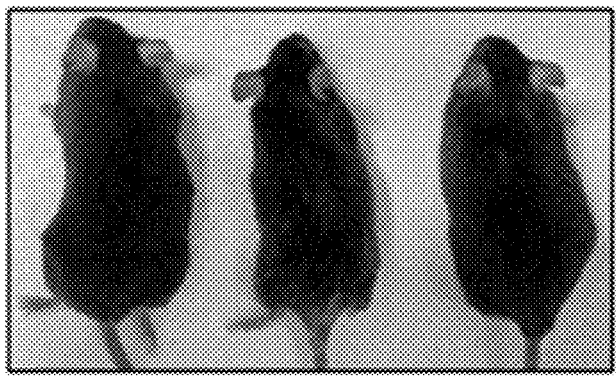
FIG. 9B shows the phenotypes of Csf1r$^{P853T/+}$ type I and Csf1r$^{P853T/+}$ type II mice.

As illustrated in FIG. 9B, in comparison to C57/BL6 mice, Csf1r$^{P853T/+}$ mice exhibit erect, shedding, and increas- ingly gray fur, coupled with a diminished mental state.

Notably, they manifest two distinctive psychological phenotypes, encompassing a depressive type (type I) and an irritable type (type II). Furthermore, as shown in FIG. 9A, both type I and type II mice exhibit reduced weight gain in contrast to their wild-type counterparts, with type I displaying the slowest growth rates (P<0.05)."

1. Three-Chamber Social Test

The foundation of the three-chamber social test lies in the innate sociability of normal mice. When faced with conspecifics, they exhibit a preference for social interaction over isolation. Furthermore, when faced with unfamiliar conspecifics, normal mice have the ability to distinguish them from familiar companions and tend to engage in more interactions with the stranger ones, demonstrating a social novelty response.

Figure 10A:
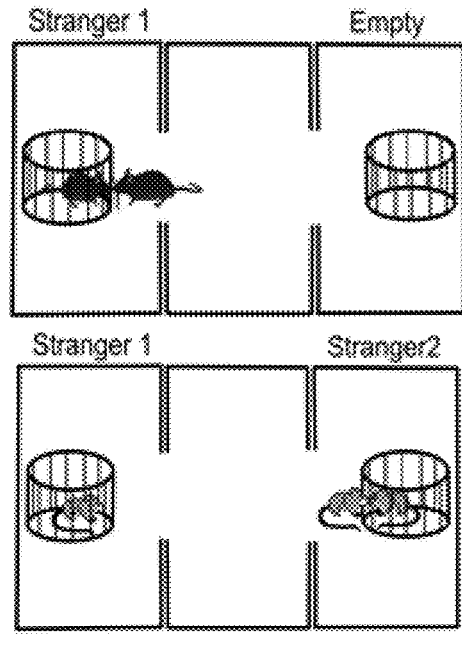
FIG. 10A is a schematic diagram of the three-chamber social test.

As shown in FIG. 10A, the three-chamber test involves dividing three chambers using transparent partitions. A Csf1r$^{P853T/+}$ mouse is placed in the central chamber and allowed to acclimate to the environment for 5 minutes.

First Phase: The partition is removed, and a cage containing an unfamiliar C57/BL6 mouse (stranger1) is placed in the left chamber, while an empty cage is placed in the right chamber. A 10-minute timer is started, and the time Csf1r$^{P853T/+}$ mouse spends in each chamber (with all four limbs inside as the criteria) is recorded.

Second Phase: The empty cage in the right chamber is replaced with another unfamiliar C57/BL6 mouse (stranger2), and once again, the time and frequency of entry by the Csf1r$^{P853T/+}$ mouse into the right chamber are recorded. After testing one mouse, the apparatus is cleaned with 10% alcohol.

The test is repeated three times, and the same test setup is also prepared for C57/BL6 mice as a control.

2. Maze Test

Figure 11A:
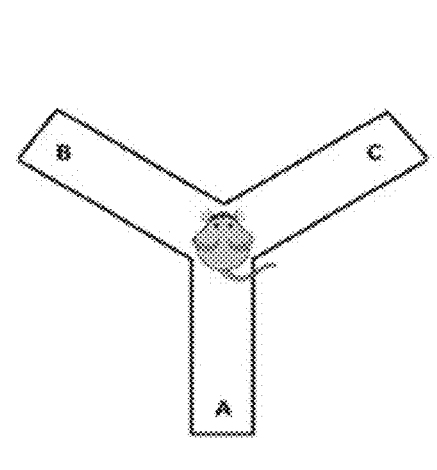
FIG. 11A is a schematic diagram of the Y-maze.

As illustrated in FIG. 11A, a Y-maze is consisted of three arms: the novel arm, the start arm, and the other arm. Novel Arm: The novel arm is blocked off by partitions in the first phase of the test, and is opened in the second phase (i.e., the testing period). Start Arm: The start arm is the arm where the mouse is placed at the beginning of the maze test. Throughout the entire test, both the start arm and the other arm remain open.

First Phase: This is the training period. The novel arm is blocked off with partitions, and the Csf1r$^{P853T/+}$ mouse is introduced into the maze from the start arm. The mouse is allowed to freely explore both the start arm and the other arm for 10 minutes. The next phase begins 1 hour later.

Second Phase: This is the testing period. The partition blocking the novel arm is removed, and the Csf1r$^{P853T/+}$ mouse is placed in the maze from the start arm. The mouse is given 5 minutes to freely explore all three arms. The time spent in each arm and the number of shuttle movements within the 5-minute period are recorded. Each consecutive entry into all three arms of the Y-maze is counted as one shuttle.

The test is repeated three times, and the same test setup is also prepared for C57/BL6 mice as a control.

3. Nest-Building Test

On the testing day in the evening, clean cotton of the same mass is provided to the Csf1r$^{P853T/+}$ mice using sterile forceps. After 24 hours, photographs are taken to record the condition of nest-building, and a scoring system for the nest-building is employed for evaluation, as follows:

5 points: Over 90% of the cotton pieces are torn into shreds, forming a complete nest with edges higher than half the height of a curled-up mouse;

4 points: Over 90% of the cotton pieces are torn, creating a flat nest with edges not exceeding half the height of a curled-up mouse;

3 points: 50%-90% of the cotton pieces are torn, but no nest is formed; cotton pieces are scattered throughout the cage;

2 points: 50%-90% of the cotton pieces remain untorn and intact;

1 point: Over 90% of the cotton pieces remain untouched and undamaged.

The test is repeated three times, and the same test setup is also prepared for C57/BL6 mice as a control.

4. Prepulse Inhibition Test

Figure 16A:
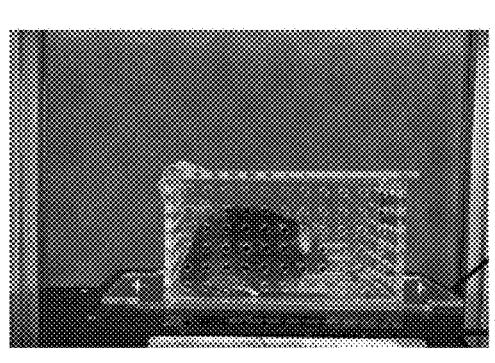
FIG. 16A shows the PPI (pre-pulse inhibition) test.
Figure 16B:
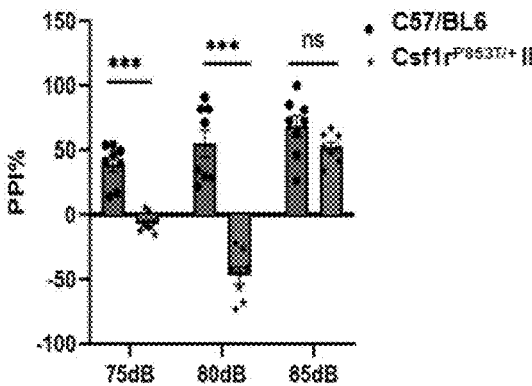
FIG. 16B shows the results of the PPI test for C57/BL6, and Csf1r$^{P853T/+}$ type I mice.

As illustrated in FIG. 16A, Csf1r$^{P853T/+}$ mice are acclimated for 5 minutes in a testing chamber with a background noise level of 62 dB to reduce interference from background noise. Subsequently, the following prepulse stimuli are administered:

Block 1: Ten shock stimuli at 120 dB.

Block 2 includes the following six modes:

(1) Background noise at 62 dB only.

(2) Shock stimulus at 120 dB only.

(3) Prepulse stimuli at 74 dB, 78 dB, or 86 dB only.

(4)-(6) Prepulse stimuli at 74 dB, 78 dB, and 86 dB, followed by a 100 ms interval and a 120 dB shock stimulus. A total of 40 shock stimuli are presented to assess the mouse's PPI strength. These six modes are presented in a pseudo-randomized order, ensuring that the prepulse-only mode (Mode (3)) occurs once every 6 trials with intervals of 10-20 seconds between adjacent modes.

Block 3 is similar to Block 1 and serves as an adaptive contrast to analyze whether the mice exhibit adaptation during the test. After collecting the startle response amplitude data, Shanghai Xinruan VisuStartle Startle Reflex Test Software is employed for data processing and analysis. Prepulse Inhibition Efficiency (PPI %) is used to represent the strength of PPI, calculated as follows: PPI %=(startle response amplitude to shock stimulus–startle response amplitude to prepulse combined with shock stimulus) ÷startle response amplitude to shock stimulus×100%. The startle response amplitude to shock stimulus is the mean response amplitude induced under shock stimulus conditions in Block 1, while the startle response amplitude to prepulse combined with shock stimulus is the mean response amplitude induced under certain prepulse intensity combined with shock stimulus conditions in Block 2.

The test is repeated three times, and the same test setup is also prepared for C57/BL6 mice as a control.

Figure 10B:
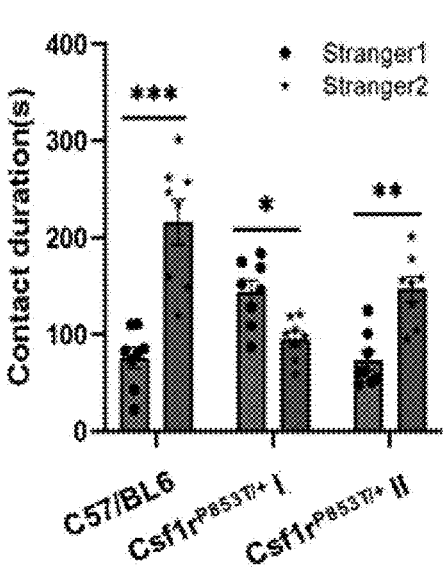
FIG. 10B shows the results of the three-chamber social test for C57/BL6, Csf1r$^{P853T/+}$ type I, and Csf1r$^{P853T/+}$ type II mice.
Figure 11B:
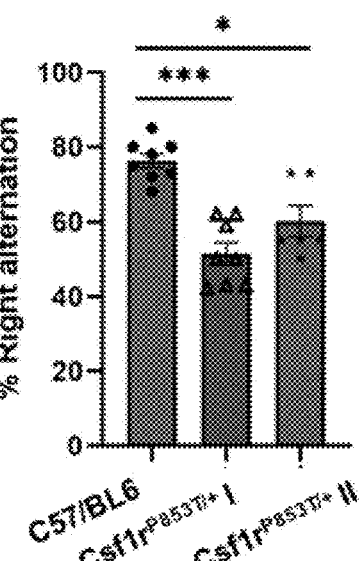
FIG. 11B shows the results of the Y-maze test for C57/BL6, Csf1r$^{P853T/+}$ type I, and Csf1r$^{P853T/+}$ type II mice.
Figure 13A:
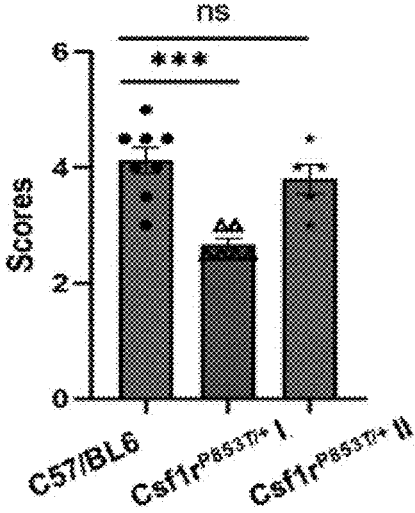
FIG. 13A shows the nest-building test for C57/BL6, Csf1r$^{P853T/+}$ type I, and Csf1r$^{P853T/+}$ type II mice.
Figure 13B:
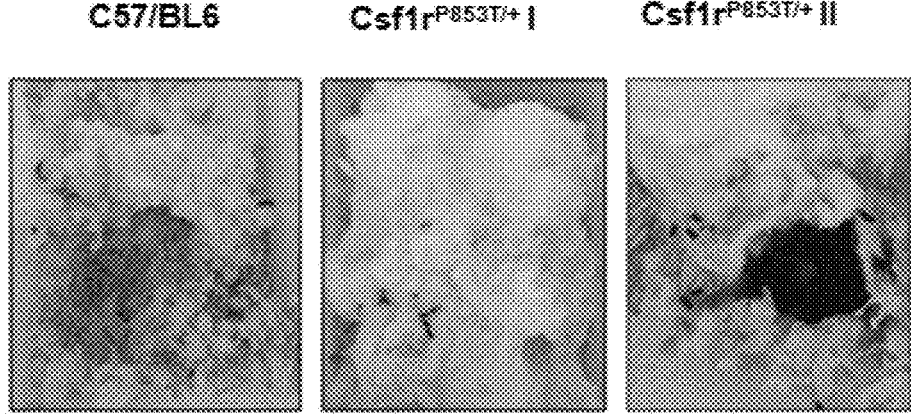
FIG. 13B shows the nest-building results for C57/BL6, Csf1r$^{P853T/+}$ type I, and Csf1r$^{P853T/+}$ type II mice.

As shown in FIG. 10B, results from the Three-Chamber Social Test indicate that Csf1r$^{P853T/+}$ type I mice spent more time exploring stranger1, but significantly less time exploring stranger2, with the time spent exploring stranger2 being significantly lower than that spent exploring stranger1. Csf1r$^{P853T/+}$ type II mice spent significantly less time exploring stranger1 than stranger2. In FIG. 11B, results from the Y-Maze Test demonstrate that both Csf1r$^{P853T/+}$ type I and type II mice had significantly reduced instances of correct exploration compared to wild-type C57/BL6 mice. As shown in FIGS. 13A and 13B, results from the Nest-Building Test reveal that Csf1r$^{P853T/+}$ type I mice exhibited a significantly reduced nest-building score, while Csf1r$^{P853T/+}$ type II mice did not show a significant reduction. In FIG. 10B, results from the Prepulse Inhibition Test indicate that Csf1r$^{P853T/+}$ type II mice had a significantly reduced prepulse inhibition rate compared to wild-type C57/BL6 mice.

Example 3: Motor Function Assessment of Csf1r$^{P853T/+}$ Mice

1. Open Field Test

Csf1r$^{P853T/+}$ mice are gently removed from their housing cages and placed quickly into an open field arena measuring 50×50×25 centimeters. During placement, care is taken to ensure that all mice are oriented in the same direction within the arena. The tracking system is then activated to automatically record the mice's movement distance, resting time, and active time over a 15-minute test period.

The test is repeated three times, and the same test setup is also prepared for C57/BL6 mice as a control.

2. Rotarod Test

Figure 14A:
FIG. 14A shows the rotarod test.

As illustrated in FIG. 14A, the rotarod apparatus is prepared with the rotation speed set and power supply activated, causing the rod to rotate automatically. Csf1r$^{P853T/+}$ mice are placed on the rotarod instrument with a constant rotation speed of 15 revolutions per minute (r/min) for continuous training over three days. On the fourth day, three consecutive trials are conducted, each lasting for 5 minutes. A 30-minute rest period is observed between each trial, and the time spent by the mice on the rotarod during the three trials on the fourth day is recorded for analysis.

The same test setup is also prepared for C57/BL6 mice as a control.

3. Gait Analysis

In the seven days preceding the gait test, Csf1r$^{P853T/+}$ mice are trained. These mice are allowed to freely run from one side of a corridor to the other, with one session per day, consisting of 6 runs per session. As training progresses, the exploratory behavior of Csf1r$^{P853T/+}$ mice within the corridor decreases. By the seventh day, most Csf1r$^{P853T/+}$ mice can traverse the corridor continuously without pauses. Mice that still cannot cross the corridor without interruptions are excluded from the experiment. On the eighth day, Csf1r$^{P853T/+}$ mice are placed in the corridor, and their gait is recorded and measured as they freely run from one side to the other for 4 runs.

The same test setup is also arranged for C57/BL6 mice as a control.

Figure 12A:
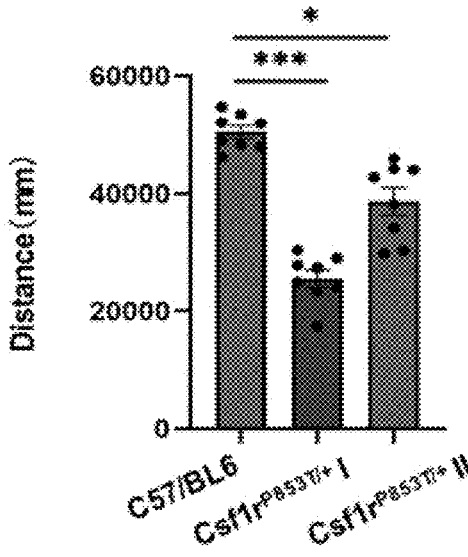
FIG. 12A shows the results of the open-field test for C57/BL6, Csf1r$^{P853T/+}$ type I, and Csf1r$^{P853T/+}$ type II mice.
Figure 12B:
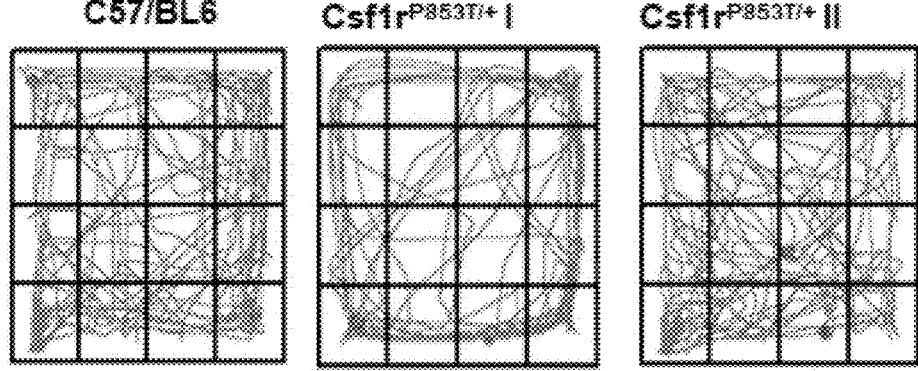
FIG. 12B shows the route map of the open-field test for C57/BL6, Csf1r$^{P853T/+}$ type I, and Csf1r$^{P853T/+}$ type II mice.
Figure 14B:
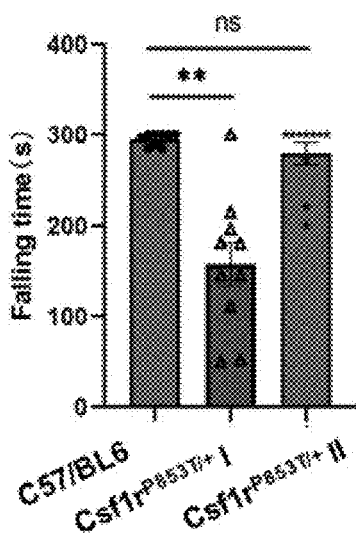
FIG. 14B shows the results of the rotarod test for C57/BL6, Csf1r$^{P853T/+}$ type I, and Csf1r$^{P853T/+}$ type II mice.
Figure 15A:
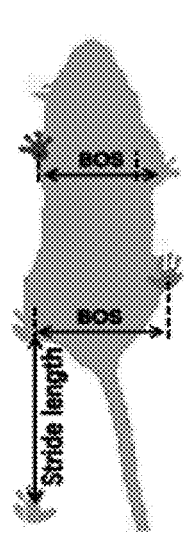
FIG. 15A shows the stride calculation pattern.
Figure 15B:
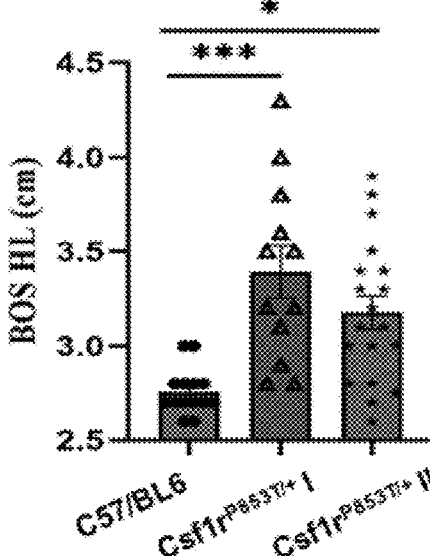
FIG. 15B shows the results of the gait test for C57/BL6, Csf1r$^{P853T/+}$ type I, and Csf1r$^{P853T/+}$ type II mice.

As shown in FIGS. 12A and 12B, the open-field test results indicate that both Csf1r$^{P853T/+}$ type I and Csf1r$^{P853T/+}$ type II mice exhibit a significant reduction in total traveled distance compared to wild-type mice. As shown in FIG. 14B, the rotarod experiment results reveal that Csf1r$^{P853T/+}$ type I mice significantly decrease their time spent on the rod, while Csf1r$^{P853T/+}$ type II mice show no significant reduction. As shown in FIG. 15B, the gait analysis results demonstrate that both Csf1r$^{P853T/+}$ type I and Csf1r$^{P853T/+}$ type II mice exhibit a significant increase in the distance between their hind paws when compared to wild-type mice.

Example 4: Pathological Expression of Csf1r in Csf1r$^{P853T/+}$ Mice

1. Immunohistochemistry Experiment

Following the completion of behavioral tests, the mice from each group are anesthetized. A 30 mL injection of normal saline is administered through the left ventricle of the heart, followed by systemic fixation with 4% PFA. The mice are then decapitated, and the entire brain is collected. The whole brain is sequentially immersed in 15%, 20%, and 30% sucrose solutions and subsequently frozen-sectioned to obtain 25 km-thick slices. The slices are subjected to a 15-minute incubation in 3% $H_2O_2$, followed by washing with PBS three times. Subsequently, after a 30-minute incubation with normal blocking serum, the primary antibody (Servicebio, GB11581) is added and incubated overnight at 4° C. with gentle agitation. The slices are then washed with PBS three times, followed by a 1-hour incubation at room temperature with the secondary antibody (Servicebio, GB23303). After another three washes with PBS, visualization of CSF1R expression in the striatum area of the mice from each group is achieved using the diaminobenzidine (DAB) method. The expression is observed under a light microscope.

2. Hematoxylin and Eosin (HE) Staining

After the completion of behavioral tests, the mice from each group are anesthetized. A 30 mL injection of normal saline is administered through the left ventricle of the heart, followed by systemic fixation with 4% PFA. The mice are then decapitated, and the entire brain is collected. The whole brain is sequentially immersed in 15%, 20%, and 30% sucrose solutions and subsequently frozen-sectioned to obtain 25 km-thick slices. These slices are fixed in 4% paraformaldehyde and allowed to air dry naturally. The subsequent steps for HE staining are as follows:

| | |
|---|---|
| Distilled water | 1 minute |
| Hematoxylin staining solution | 5-15 minutes |
| Brief rinse under running water to remove excess hematoxylin | 1-3 seconds |
| 1% hydrochloric acid in ethanol | 1-3 seconds |
| Brief rinse under running water | 10-30 seconds |
| Eosin staining solution | 10-30 seconds |
| Rinse under running water | 10-15 minutes |
| Distilled water rinse | 1-2 seconds |
| 0.5% alcoholic eosin solution | 1-3 minutes |
| Distilled water rinse | 1-2 seconds |
| 95% ethanol | 3-5 minutes |
| Xylene (I) | 5 minutes |
| Xylene (II) | 5 minutes |

Mount with neutral mounting medium

Results: Cytoplasm appears red, and cell nuclei appear blue-purple.

3. Luxol Fast Blue (LFB) Staining

After the completion of behavioral tests, the mice from each group are anesthetized. A 30 mL injection of normal saline is administered through the left ventricle of the heart, followed by systemic fixation with 4% PFA. The mice are then decapitated, and the entire brain is collected. The whole brain is sequentially immersed in 15%, 20%, and 30% sucrose solutions and subsequently frozen-sectioned to obtain 25 km-thick slices. These slices are immediately fixed in 4% paraformaldehyde and allowed to air dry naturally. Following rinsing with distilled water, the sections are immersed in a 0.1% LFB (Luxol Fast Blue) solution, sealed, and left to soak at 60° C. for 8-16 hours. Afterward, they are rinsed again with distilled water and then immersed in 95% alcohol. Subsequently, a 0.05% lithium carbonate solution is used for staining, with the sections being stained for at least 10 seconds. Further differentiation is achieved by continued exposure to 70% alcohol until a clear distinction between gray and white matter is observed under the microscope. Following a rinse with distilled water, a few drops of a 0.25% cresyl violet solution mixed with ice acetic acid staining solution are applied for a 10-minute secondary staining, and the color is further differentiated using 70% alcohol until the cell nuclei and Nissl bodies appear in red.

Figure 17:
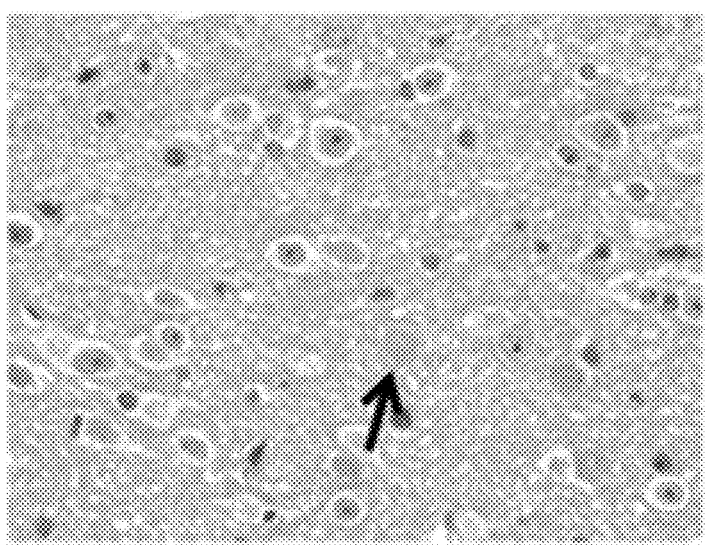
FIG. 17 shows HE (Hematoxylin and Eosin) staining of the cortex in for C57/BL6 and Csf1r$^{P853T/+}$ mice, with arrowheads pointing to axonal spheroid-like changes.
Figure 18:
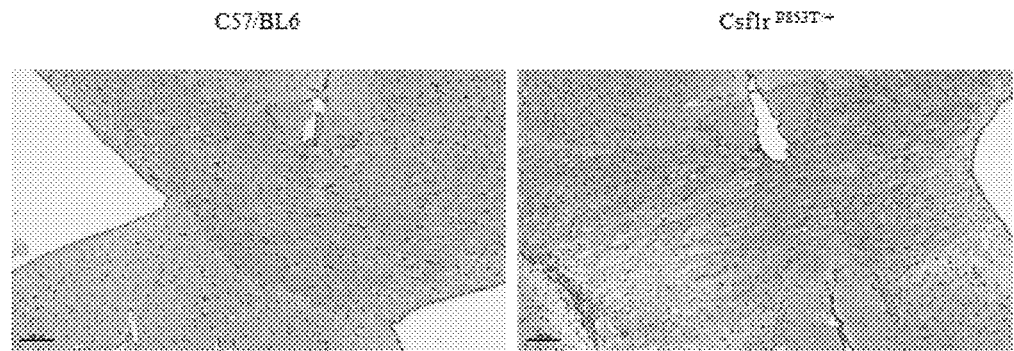
FIG. 18 shows HE staining of the corpus callosum in C57/BL6 and Csf1r$^{P853T/+}$ mice.
Figure 19:
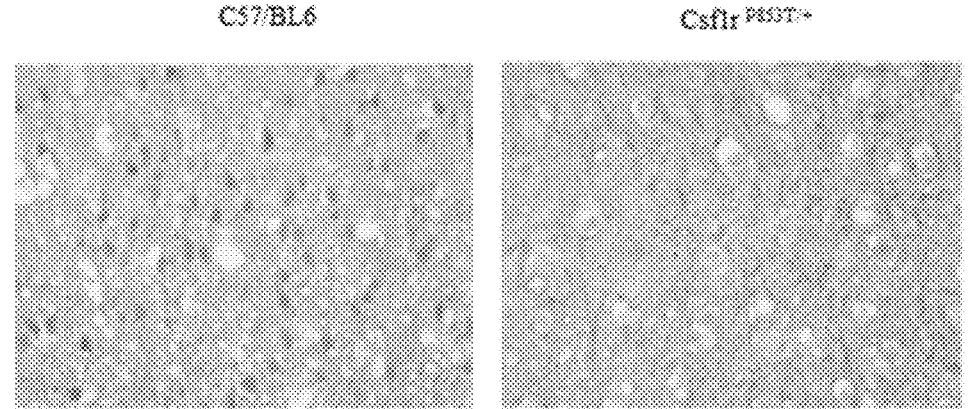
FIG. 19 shows LFB (Luxol Fast Blue) staining of the cortex in C57/BL6 and Csf1r$^{P853T/+}$ mice.
Figure 20:
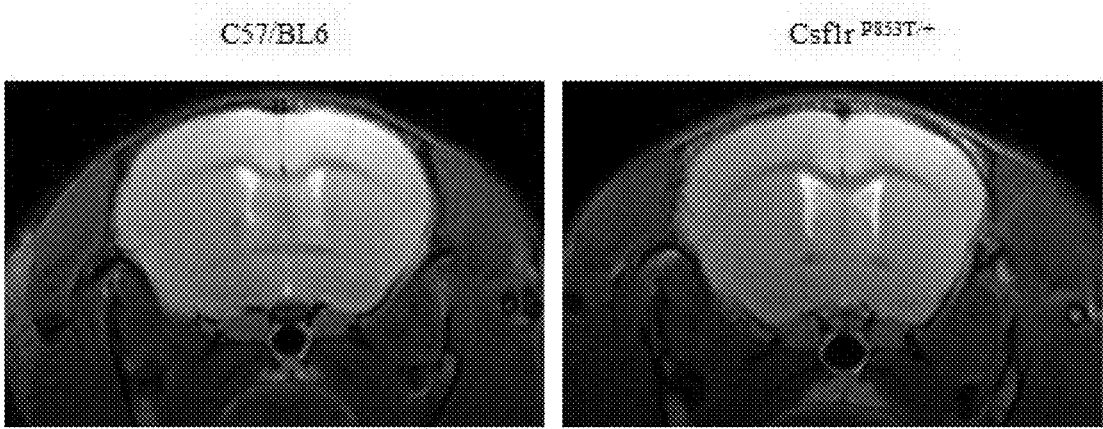
FIG. 20 shows MRI-T2 phase imaging of C57/BL6 and Csf1r$^{P853T/+}$ mice.
Figure 21:
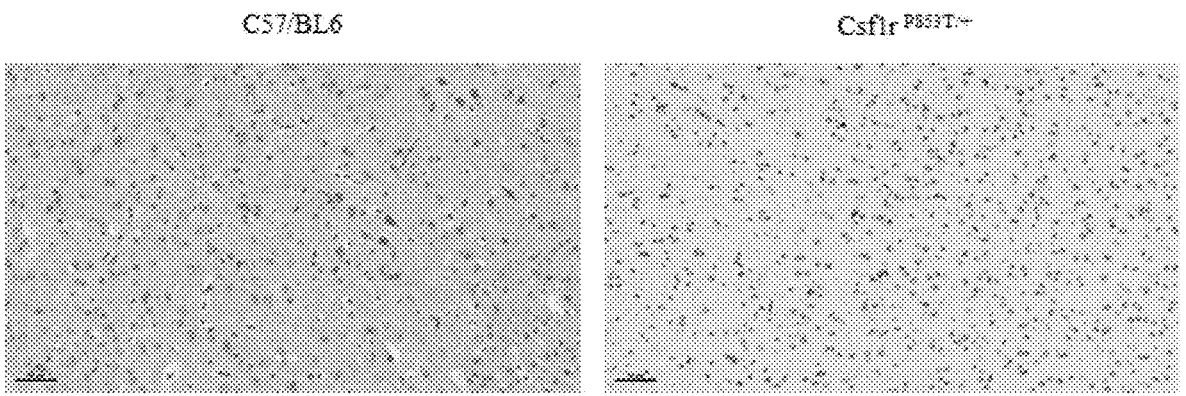
FIG. 21 shows the immunohistochemical results of CD68 staining in the cortex region of C57/BL6 and Csf1r$^{P853T/+}$ mice.
Figure 22:
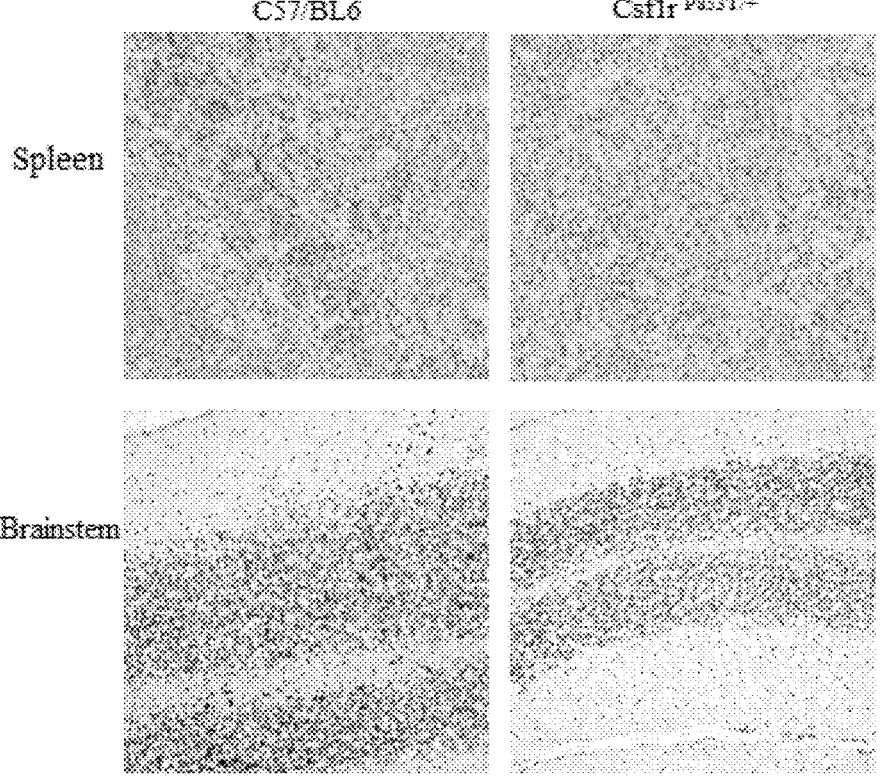
FIG. 22 shows the expression of Csf1r in the spleen and brainstem of C57/BL6, and Csf1r$^{P853T/+}$ mice.

As shown in FIG. 22, compared to wild-type mice, Csf1r$^{P853T/+}$ mice exhibit a significant reduction in Csf1r-positive cells in the spleen and brainstem. As shown in FIGS. 17, Csf1r$^{P853T/+}$ mice display extensive white matter degeneration with typical axonal spheroid-like changes. As shown in FIGS. 18 and 20, compared to wild-type mice, Csf1r$^{P853T/+}$ mice exhibit demyelination, thinning of the corpus callosum, enlargement of ventricles. Luxol Fast Blue (LFB) staining, as shown in FIG. 19, shows lipid and phospholipid-filled macrophages in Csf1r$^{P853T/+}$ mice, which are absent in wild-type mice. FIG. 21 shows a significant increase in CD68-positive cells in Csf1r$^{P853T/+}$ mice compared to wild-type mice.

---

What is claimed is:

1. A mutated Csf1r (Colony stimulating factor 1 receptor) gene, wherein the mutated Csf1r gene is obtained by changing 2557th nucleotide of a Csf1r gene from C to A; the mutated Csf1r gene is shown in SEQ ID NO: 1.

2. A mutated Csf1r protein, wherein the mutated Csf1r protein is encoded by the mutated Csf1r gene of claim 1; the mutated Csf1r protein is obtained by substituting proline with threonine at the 853rd amino acid position of a Csf1r protein; the amino acid sequence of the mutated Csf1r protein is shown in SEQ ID NO: 2.

3. An expression cassette, recombinant virus, recombinant cell, recombinant bacteria, or recombinant vector, comprising the mutated Csf1r gene of claim 1.

4. A method for constructing a murine model with mutations in Csf1r gene, comprising the following steps:
(1) constructing a targeting vector, $Csf1r^{P853T/+}$, containing the mutated Csf1r gene of claim 1;
(2) electroporating the targeting vector $Csf1r^{P853T/+}$ obtained in step (1) into mouse embryonic stem cells and verifying positive clones;
(3) injecting the verified positive mouse embryonic stem cells from step (2) into blastocysts and transplanting the blastocysts into the uteri of female mice to obtain F0 generation mice;
(4) breeding the F0 generation mice obtained in step (3) with mice that express Cre enzyme in a tissue-specific manner and selecting F1 generation heterozygous mice that carry both the point mutation in step (1) and the Cre gene in their genomes;

(5) pairing two heterozygous F1 generation mice obtained in step (4) and selecting F2 generation homozygous mice, thereby obtaining the desired murine model.

5. The method according to claim 4, wherein the mice that express Cre enzyme specifically in tissues are mice that express Cre enzyme in macrophages.

6. The method according to claim 4, wherein the F2 generation homozygous mice are mice afflicted with brain diseases caused by microglial dysfunction.

* * * * *

SEQUENCE LISTING

```
Sequence total quantity: 13
SEQ ID NO: 1           moltype = DNA  length = 2934
FEATURE                Location/Qualifiers
source                 1..2934
                       mol_type = other DNA
                       organism = synthetic construct
SEQUENCE: 1
atggagttgg ggcctcctct ggtcctgctg ctggccacag tttggcatgg tcaggggggcc  60
cctgtcatcg agcctagtgg cccagaactg gttgtagagc cgggtgaaac ggtgaccctg  120
cgatgtgtga gcaatggcag tgtggaatgg gatggcccca tctctcccta ctggaccttg  180
gaccctgaat ctcccggaag caccctgacc acaagaaacg cgaccttcaa aaacactggg  240
acctaccgtt gtaccgagct tgaagacccc atggcaggca gtaccaccat ccacttgtat  300
gtcaaagatc cggcccactc ttggaatttg ctggcacagg aggtgacagt ggttgagggc  360
caggaagctg tgctgccctg tctgatcact gaccctgcac tgaaggacag tgtctcactg  420
atgcgtgagg ggggcaggca ggtcttacgc aaaacggtct acttcttctc gccatggcga  480
gggttcatta tccgcaaggc taaagtcctt gacagcaata cctacgtgtg caagaccatg  540
gtgaatggta gggaatccac ctccactggc atctggctta aggtgaatcg agtccaccca  600
gagcccccac agataaaatt ggagcctagc aagctggtgc ggattcgagg ggaggctgcg  660
cagatcgtgt gctcggccac taacgccgaa gtgggattca acgttatcct caaacgtgga  720
gacaccaagc tggaaatccc cctaaacagt gacttccaag ataactatta taaaaaagtc  780
cgggctctca gtctcaacgc tgtggacttc caagacgctg gcatatattc ttgtgtggcc  840
agcaatgatg ttggcacacg cacggccacc atgaacttcc aggtggtgga gagtgcctac  900
ttaaacttga cctctgagca gagcctcttg caggaggtgt ctgtgggtga cagcctcatc  960
ctcacggtcc atgcagatgc ctaccctagc atacagcatt acaactggac ctacctaggt  1020
ccattctttg aagaccagcg caagcttgag tttatcaccc aaagggccat atacaggtac  1080
acattcaagc tcttctctgaa ccgtgtaaag gcctcagagg cgggccagta cttcttaatg  1140
gcacaaaaca aggcaggctg gaataatctg acctttgagc tcaccctgcg atatccccca  1200
gaggtcagtg ttacatggat gcctgtgaat ggctctgatg tcctgttctg tgacgtctct  1260
gggtaccctc agcccagcgt gacatggatg gagtgcaggg gccacaccga taggtgtgat  1320
gaagcccagg ctttgcaggt ttggaatgac acccaccctg aagtcctgag tcagaagccc  1380
ttcgacaaag tgatcattca gagccagctg cccattggga ccttaaaaca caacatgact  1440
tatttttgca aaacccacaa cagtgtgggg aacagctctc agtacttcag ggccgtctcc  1500
ctaggacaaa gcaagcagct ccccgatgag tccctcttca ctccggtggt ggtggcctgt  1560
atgtctgtca tgtctctgct ggtgctactg ctgttgctgc tcttgtacaa gtacaagcag  1620
aagccgaagt accaggtgcg ctggaagatc atcgagagat acgaaggcaa tagctacacc  1680
ttcattgacc ctactcagtt gcectacaat gagaagtgag agttccctcg gaacaacctg  1740
cagtttggta agactctagg agccggtgcc tttgggaagg tggtggaggc tacagcettt  1800
ggtctgggca agaagatgc agtgctgaag gtggctgtga agatgctaaa gtccacggct  1860
catgctgatg agaaggaggc cctgatgtca gagctgaaga tcatgagtca cctgggacag  1920
cacgagaata tagtcaacct cttgggagcc tgtactcacg gaggacctgt cctggtcatc  1980
actgaatact gctgctatgg agacctactc aactttctcc gaaggaaggc cgaggctatg  2040
ctaggaccca gcctgagtcc tggtcaggac tccgaggggag actccagcta caagaacatc  2100
cacctggaga agaaatatgt gcgcagggac agtggcttct ccagtcaggg tgtagacacc  2160
tacgtggaga tgaggcctgt ctcgacttct tcaagtgact ccttctttaa gcaagatctg  2220
gacaaagagg ccagccggcc cctggagctc tgggacctgc tccacttctc cagccaagtg  2280
gctcagggca tggcettcct tgcttctaaa aactgcatcc accgggacgt agcagctcga  2340
aacgtgctgt tgaccagcgg acatgtggcc aagattgggg actttggact ggctagggac  2400
atcatgaatg actccaacta tgttgtcaag ggcaatgccc gcctgcctgt aaagtggatg  2460
gccccagaga gcatctttga ctgcgtctac acagttcaga gtgatgtgtg gtcctacggc  2520
atcctcctct gggagatctt ctcgcttggt ctgaacacct accccggcat cctagtgaac  2580
aacaagttct acaaactggt gaaggatgga taccaaatgg cccagcctgt atttgcaccg  2640
aagaacatat acagcatcat gcagtcctgc tgggacctgg agcctaccag aagacccacc  2700
ttccaacaga tctgcttcct cctccaggag caggcccgac tggagaggag agaccaggac  2760
tatgctaacc tgccaagcag cggtggcagc agcggcagtg acagtggtgg tggcagcagc  2820
ggtggcagca gcagtgagcc agaagaggag agctccagtg aacacctggc ctgctgtgag  2880
ccagggggaca tcgcccagcc cctgctgcag cctaacaact accagttctg ctga       2934

SEQ ID NO: 2           moltype = AA  length = 977
FEATURE                Location/Qualifiers
source                 1..977
                       mol_type = protein
                       organism = synthetic construct
SEQUENCE: 2
MELGPPLVLL LATVWHGQGA PVIEPSGPEL VVEPGETVTL RCVSNGSVEW DGPISPYWTL  60
DPESPGSTLT TRNATFKNTG TYRCTELEDP MAGSTTIHLY VKDPAHSWNL LAQEVTVVEG  120
QEAVLPCLIT DPALKDSVSL MREGGRQVLR KTVYFFSPWR GFIIRKAKVL DSNTYVCKTM  180
VNGRESTSTG IWLKVNRVHP EPPQIKLEPS KLVRIRGEAA QIVCSATNAE VGFNVILKRG  240
DTKLEIPLNS DFQDNYYKKV RALSLNAVDF QDAGIYSCVA SNDVGTRTAT MNFQVVESAY  300
LNLTSEQSLL QEVSVGDSLI LTVHADAYPS IQHYNWTYLG PFFEDQRKLE FITQRAIYRY  360
```

-continued

```
TFKLFLNRVK ASEAGQYFLM AQNKAGWNNL TFELTLRYPP EVSVTWMPVN GSDVLFCDVS    420
GYPQPSVTWM ECRGHTDRCD EAQALQVWND THPEVLSQKP FDKVIIQSQL PIGTLKHNMT    480
YFCKTHNSVG NSSQYFRAVS LGQSKQLPDE SLFTPVVVAC MSVMSLLVLL LLLLLYKYKQ    540
KPKYQVRWKI IERYEGNSYT FIDPTQLPYN EKWEFPRNNL QFGKTLGAGA FGKVVEATAF    600
GLGKEDAVLK VAVKMLKSTA HADEKEALMS ELKIMSHLGQ HENIVNLLGA CTHGGPVLVI    660
TEYCCYGDLL NFLRRKAEAM LGPSLSPGQD SEGDSSYKNI HLEKKYVRRD SGFSSQGVDT    720
YVEMRPVSTS SSDSFFKQDL DKEASRPLEL WDLLHFSSQV AQGMAFLASK NCIHRDVAAR    780
NVLLTSGHVA KIGDFGLARD IMNDSNYVVK GNARLPVKWM APESIFDCVY TVQSDVWSYG    840
ILLWEIFSLG LNTYPGILVN NKFYKLVKDG YQMAQPVFAP KNIYSIMQSC WDLEPTRRPT    900
FQQICFLLQE QARLERRDQD YANLPSSGGS SGSDSGGGSS GGSSSEPEEE SSSEHLACCE    960
PGDIAQPLLQ PNNYQFC                                                  977

SEQ ID NO: 3            moltype = DNA   length = 2934
FEATURE                 Location/Qualifiers
source                  1..2934
                        mol_type = other DNA
                        organism = synthetic construct
SEQUENCE: 3
atggagttgg ggcctcctct ggtcctgctg ctggccacag tttggcatgg tcaggggggc    60
cctgtcatcg agcctagtgg cccagaactg gttgtagagc cgggtgaaac ggtgaccctg    120
cgatgtgtga gcaatggcag tgtggaatgg gatggcccca tctctcccta ctggaccttg    180
gaccctgaat ctcccggaag caccctgacc acaagaacgc cgaccttcaa aaacactggt    240
acctaccgtt gtaccgagct tgaagacccc atggcaggca gtaccaccat ccacttgtat    300
gtcaaagatc cggcccactc ttggaatttg ctggcacagg aggtgacagt ggttgagggc    360
caggaagctg tgctgccctg tctgatcact gaccctgcac tgaaggacag tgtctcactg    420
atgcgtgagg ggggcaggca ggtcttacgc aaaacggtct acttcttctc gccatggcga    480
gggttcatta ccgcaaggc taaagtcctt gacagcaata cctacgtgtg caagaccatg    540
gtgaatggta gggaatccac ctccactggc atctggctta aggtgaatcg agtccaccca    600
gagcccccac agataaaatt ggagcctagc aagctggtgc ggattcgagg ggaggctgcg    660
cagatcgtgt gctcggccac taacgccgaa gtgggattca acgttatcct caaacgtgga    720
gacaccaagc tggaaatccc cctaaacagt gacttccaag ataactatta taaaaaagtc    780
cgggctctca gtctcaacgc tgtggacttc caagacgctg gcatatattc ttgtgtggcc    840
agcaatgatg ttggcacacg cacggccacc atgaacttcc aggtggtgga gagtgcctac    900
ttaaacttga cctctgagca gagcctcttg caggaggtgt ctgtgggtga cagcctcatc    960
ctcacggtcc atgcagatgc ctaccctagc atacagcatt acaactggac ctacctaggt   1020
ccattctttg aagaccagcg caagcttgag tttatcaccc aaaggggccat atacaggtac   1080
acattcaagc tctttctgaa ccgtgtaaag gcctcagagg cgggccagta cttcttaatg   1140
gcacaaaaca aggcaggctg gaataatctg acctttgagc tcaccctgcg atatccccca   1200
gaggtcagtg ttacatggat gctgtgaat ggctctgatg tcctgttctg tgacgtctct   1260
gggtaccctc agcccagcgt gacatggatg gagtgcaggg gccacaccga taggtgtgat   1320
gaagcccagg ctttgcaggt ttggaatgac acccaccctg aagtcctgag tcagaagccc   1380
ttcgacaaag tgatcattca gagccagctg cccattggga ccttaaaaca caacatgact   1440
tattttgca aaacccacaa cagtgtgggt aacagctctc agtacttcag ggccgtctca   1500
ctaggacaaa gcaagcagct ccccgatgag tccctcttca ctccggtggt ggtggcctgt   1560
atgtctgtca tgtctctgct ggtgctactg ctgttgctgc tcttgtacaa gtacaagcag   1620
aagccgaagt accaggtgcg ctggaagatc atcgagagat acgaaggcaa tagctacacc   1680
ttcattgacc ctactcagtt gccctacaat gagaagtggg agttccctcg gaacaacctg   1740
cagtttggta agactctagg agccggtgcc tttgggaagg tggtggaggc tacagccttt   1800
ggtctgggca agaagatgc agtgctgaag gtggctgtga agatgctaaa gtccacggct   1860
catgctgatg agaaggaggc cctgatgtca gagctgaaga tcatgagtca cctgggacag   1920
cacgagaata gtcaacct cttgggagcc tgtactcacg gaggacctgt cctggtcatc   1980
actgaatact gctgctatgg agacctactc aactttctcc gaaggaaggc cgaggctatg   2040
ctaggaccca gcctgagtcc tggtcaggac tccgagggag actccagcta caagaacatc   2100
cacctggaga agaaatatgt gcgcagggac agtggcttct ccagtcaggg tgtagacacc   2160
tacgtggaga tgaggcctgt ctcgacttct tcaagtgact ccttctttaa gcaagatctg   2220
gacaaagagg ccagccggc cctggagctc tgggacctgc tccacttctc cagccaagtg   2280
gctcaggca tggccttcct tgcttctaaa aactgcatcc accgggacgt agcagctcga   2340
aacgtgctgt tgaccagcgg acatgtggcc aagattgggg actttggact ggctagggac   2400
atcatgaatg actccaacta tgttgtcaag ggcaatgccc gcctgcctgt aaagtggatg   2460
gccccagaga gcatctttga ctgcgtctac acagttcaga gtgatgtgtg gtcctacggc   2520
atcctcctct gggagatctt ctcgcttggt ctgaacccct accccggcat cctagtgaac   2580
aacaagttct acaaactggt gaaggatgga taccaaatgg cccagcctgt atttgcaccg   2640
aagaacatat acagcatcat gcagtcctgc tgggacctgg agcctaccag aagacccacc   2700
ttccaacaga tctgcttcct cctccaggag caggcccgac tggagaggag agaccaggac   2760
tatgctaacc tgccaagcag cggtggcagc agcggcagtg acagtggtgg tggcagcagc   2820
ggtggcagca gcagtgagcc agaagaggag agctccagtg aacacctggc ctgctgtgag   2880
ccaggggaca tcgcccagcc cctgctgcag cctaacaact accagttctg ctga         2934

SEQ ID NO: 4            moltype = AA   length = 977
FEATURE                 Location/Qualifiers
source                  1..977
                        mol_type = protein
                        organism = synthetic construct
SEQUENCE: 4
MELGPPLVLL LATVWHGQGA PVIEPSGPEL VVEPGETVTL RCVSNGSVEW DGPISPYWTL     60
DPESPGSTLT TRNATFKNTG TYRCTELEDP MAGSTTIHLY VKDPAHSWNL LAQEVTVVEG    120
QEAVLPCLIT DPALKDSVSL MREGGRQVLR KTVYFFSPWR GFIIRKAKVL DSNTYVCKTM    180
VNGRESTSTG IWLKVNRVHP EPPQIKLEPS KLVRIRGEAA QIVCSATNAE VGFNVILKRG    240
DTKLEIPLNS DFQDNYYKKV RALSLNAVDF QDAGIYSCVA SNDVGTRTAT MNFQVVESAY    300
```

```
LNLTSEQSLL QEVSVGDSLI LTVHADAYPS IQHYNWTYLG PFFEDQRKLE FITQRAIYRY  360
TFKLFLNRVK ASEAGQYFLM AQNKAGWNNL TFELTLRYPP EVSVTWMPVN GSDVLFCDVS  420
GYPQPSVTWM ECRGHTDRCD EAQALQVWND THPEVLSQKP FDKVIIQSQL PIGTLKHNMT  480
YFCKTHNSVG NSSQYFRAVS LGQSKQLPDE SLFTPVVAC MSVMSLLVLL LLLLLYKYKQ  540
KPKYQVRWKI IERYEGNSYT FIDPTQLPYN EKWEFPRNNL QFGKTLGAGA FGKVVEATAF  600
GLGKEDAVLK VAVKMLKSTA HADEKEALMS ELKIMSHLGQ HENIVNLLGA CTHGGPVLVI  660
TEYCCYGDLL NFLRRKAEAM LGPSLSPGQD SEGDSSYKNI HLEKKYVRRD SGFSSQGVDT  720
YVEMRPVSTS SSDSFFKQDL DKEASRPLEL WDLLHFSSQV AQGMAFLASK NCIHRDVAAR  780
NVLLTSGHVA KIGDFGLARD IMNDSNYVVK GNARLPVKWM APESIFDCVY TVQSDVWSYG  840
ILLWEIFSLG LNPYPGILVN NKFYKLVKDG YQMAQPVFAP KNIYSIMQSC WDLEPTRRPT  900
FQQICFLLQE QARLERRDQD YANLPSSGGS SGSDSGGGSS GGSSSEPEEE SSSEHLACCE  960
PGDIAQPLLQ PNNYQFC                                                977

SEQ ID NO: 5            moltype = DNA   length = 17560
FEATURE                 Location/Qualifiers
source                  1..17560
                        mol_type = other DNA
                        organism = synthetic construct
SEQUENCE: 5
cgcttacaat ttccattcgc cattcaggct gcgcaactgt tgggaagggc gatcggtgcg   60
ggcctcttcg ctattacgcc agctggcgaa aggggggatg gctgcaaggc gattaagttg  120
ggtaacgcca gggttttccc agtcacgacg ttgtaaaacg aggccagtg aattgtaata  180
cgactcacta tagggcgaat tggagctcca ccgcccgggc tggttcttc cgcctcagaa  240
gccatagagc ccaccgcatc cccagcatgc ctgctattgt cttcccaatc ctccccttg  300
ctgtcctgcc ccaccccacc ccagaata gaatgacacc tactcagaca atgcgatgca  360
atttcctcat tttattagga aaggacagtg ggagtgtcac cttccagggt caaggaaggc  420
acggggagg ggcaaacaac agatggctgg caactagaag gcacagtcga ggctgatcag  480
cgagctctag gatctgcatt ccaccactgc tcccattcat cagttccata ggttggaatc  540
taaaatacac aaacaattag aatcagtagt ttaacacatt atacacttaa aaattttata  600
tttaccttag agctttaaat ctctgtaggt agtttgtcac attatgtcac accacagaag  660
taaggttcct tcacaaagag atcgcctgac acgatttcct gcacaggctt gagccatata  720
ctcatacatc gcatcttggc cacgtttcc acgggtttca aaattaatct caagttctac  780
gcttaacgct ttcgcctgtt cccagttatt aatatattca acgctagaac tcccctcagc  840
gaagggaagg ctgagcacta cacgcgaagc accatcaccg aaccttttga taaactcttc  900
cgttccgact tgctccatca acggttcagt gagacttaaa cctaactctt tcttaatagt  960
ttcggcatta tccactttta gtgcgagaac cttcgtcagt cctggatacg tcactttgac 1020
cacgcctcca gcttttccag agagcgggtt ttcattatct acagagtatc ccgcagcgtc 1080
gtatttattg tcggtactat aaaaccctt ccaatcatcg tcataatttc cttgtgtacc 1140
agattttggc ttttgtatac ctttttgaat ggaatctaca taaccaggtt tagtcccgtg 1200
gtacgaagaa aagttttcca tcacaaaaga tttagaagaa tcaacaacat catcaggatc 1260
catggcacgc gcttctacaa ggcgctggcc gaagaggtgc gggagtttca cgccaccaag 1320
atctgcggca cgctgttgac gctgttaagc gggtcgctgc agggtcgctc ggtgttcgag 1380
gccacacgcg tcaccttaat atgcgaagtg gacctcggac cgcgccgcc cgactgcatc 1440
tgcgtgttcg aattcgccaa tgacaagacg ctgggcgggg tttgctcgac attgggtgga 1500
aacattccag gcctgggtgg agaggctttt tgcttcctct tgcaaaacca cactgctcga 1560
cattgggtgg aaacattcca ggcctgggtg gagaggcttt ttgcttcctc ttgaaaacca 1620
cactgctcga tttgttagca gcctcgaatc aacccgggcg atcctaggcg atgagatcta 1680
gctgtcgcga agagtggcgc gcccagaggt tggaggactt ggaggaaatg ctggttgtcc 1740
cacagtatgt ctgcggggc cacaggacac atattccagt gaggagtggc tgatgtgtct 1800
ctacacctcc gaggggaagt gagaacagag tttattagtt gttggatgga ggtagtggaa 1860
catcctgcc tgtggcgagg ttcctagtgc actcgggcct cagttccagt tcagacaaca 1920
gagtgtttaa ccccttcaggg tcttctgctg ttctgggatt cctggaagcc accagaggct 1980
atggataaag ccatatggg aagcagagag gggaagaaac aagtttcttg ttgcccatga 2040
atcgggcaga gggggaacct gaactaagcc tgctgtttta aattggagtt tcaatattgg 2100
gtcatggtag cttgtgccct agtgctggga tcaggctgca ctcagaacca ggaaagtgta 2160
cactgtcctt atagtgtagg tattgacagc tgctgagact tggggagcta aaggtgaag 2220
aggtggcttg gctcccttct ctaagtgcat agacaggcaa agcaacaggt tcgacctatg 2280
gatcccaagt tatgctacta aagaagtatg gcttccagaa caaagagatg gtgactattc 2340
catggacact aatgggagat cctagtttct cctcctggaa gcctcaggac atggacagag 2400
tttaggtgtt gagcagctgc tgagcagctg ctgacaaacc aggcctgtct ggctgacccg 2460
cagcagtagt ggctgttggg gtaggactgt gcttctccag gtggcctgtc accatagcaa 2520
gtgtctgggt atttctgggt gttgcctgtc tacccaaacc tacagggaca tgagactctc 2580
tggggcttag atgccctgag ccaatttaag ttctgctcta gatctgggca aatttaaggc 2640
tgtgagttga ctgctctggt catggggaat attcaaacct ttccaagcga tttaaaaaaa 2700
aaaaaaaagc atgtatgagt gtgtgtctgt gtgtacctgt gttcctgctg ctcacaatgg 2760
gccaaaagat ggtgtctgct accctaggac tggggttaaa ggtgtgagcc accatgtggg 2820
tgctgggagc caaacccagt tccctctgaa tgagtagcaa gtactctcac ctgctgaggc 2880
atctctccag ccccctctct gtgcgatttt aaacttttg attttgcact tatttatctg 2940
taatgcacgt ggataagctg ggcctctctc tttccacgcg acgaccccct gggattgagc 3000
tcaggttctc aggcttggca gtcagtgcca ccctcctcga ggaactttga acgagaggct 3060
aacttgtgca atgctgtgca gagagatcag ggaaggggcc tgggactgac tcacatccca 3120
gcggggcagc tagagataac ggtcttcctg cctttgagga tgaagatcag aagaaaatcc 3180
caggagcatg ctggcattag gagcaaggaa gaactttgag caggcagaga cgcctagtga 3240
cagaaaggga tgcctctggc taaagggtgt gtctgggaag gtgtcaacgtg gcacagtgat 3300
tgctcaagtc gaatgtagca tagggcctcc cttatcagag agtgatgctc agctgacctt 3360
taggtttctt ccctctgct gagtgactaa gggaatccac aaggcagctg gagggcaatg 3420
cctgggctag gcagtgatgg gatctttccc acttctcttt cctacccagg acagtggct 3480
tctccagtca gggtgtagac acctacgtgg agatgaggcc tgtctcgact tcttcaagtg 3540
actccttctt taagcaaggt gcggaggtac cgggatgagg ggagagaagg gtgaatgggc 3600
```

-continued

```
ctaggggccg ggaactgggc ctgaggaaca gcaaggtgtg acaggggttgc cccgatgcct      3660
ttgccttcta cagatctgga caaagaggcc agccggcccc tggagctctg ggacctgctc      3720
cacttctcca gccaagtggc tcagggcatg gccttccttg cttctaaaaa cgtgagtctg      3780
ggtgggggaa aagctgaatt cctactggtc gtgggaatga ggaagaggag gcccagtgag      3840
aaagaacgga ggaatagagg aatgtacaga gggcctcaga aggcagcggg acgaagcagt      3900
acccagggca gactcctgga ggtctagcct cagccttggt atgcctgttt ctctatgtgg      3960
ccaccaacag gcttaacaat ggtttcactc agccaagcaa actagacaac agctgcttct      4020
cctcataaaa catagtcttg ttggatgagc tgtaaggatg ttggggctca gaccaccacc      4080
ctcagagcac tctagagggg caatggtgtg acttctggct cttctctttg ctatgacaat      4140
ttaggttctg taagcctcag ggtctgtgtc tgcaaactgg gatgcatata acttcgtata      4200
gcatacatta tacgaagtta ttatttgcag gaattgttta ggggtctaac gggttgttgt      4260
gtatgcaaat gcttgggaaa gcacctggta ttgtgtactt ggaggtggca gctgttggtg      4320
ttgtgtatga ggtgggccac aggctgctca cagcacaggg actcattgcc tctgaggcag      4380
gagcagccct gtggctccaa gggccagagg gccattgaaa acagggctgt ggggctagaa      4440
ttctaaatgt taaattgtcc acatcaaatc gtctcagacc tcaggcctgc acaggtttag      4500
acaggagtag acagtagact accaaaacct gcatctactt caacagagac ccaagacctc      4560
ctgctcctcc tctggtcctc aggcctcagg gaaggataaa ctgactaata atctctctgc      4620
gctttcttca gtgcatccac cgggacgtag cagctcgaaa cgtgctgttg accagcggac      4680
atgtggccaa gattggggac tttggactgg ctagggacat catgaatgac tccaactatg      4740
ttgtcaaggg caatgtgagt gccgagagag agagagagag agggagggag agagagagag      4800
agagagagag agagagagag agagagagag agagagagag agagagagag agagattgag      4860
attggttggg caggctgtgg agagcccttg actgacatgg tactgtcttg tcaggcccgc      4920
ctgcctgtaa agtggatggc cccagagagc atctttgact gcgtctacac agttcagagt      4980
gatgtgtggt cctacggcat cctcctctgg gagatcttct cgcttggtga gctgctaagc      5040
ctgttttcag gtgcagccta gggctgaccc gtctttggct atgccatcgg tgtcttgaac      5100
ctcatgacg aaatctactc aaagatgtcg gtgtccaaga cagagcaagg gctggcagga      5160
gcaatgggat ggtgagggct cttgaaccag tactgcagca cctgtgtgta attcagaccc      5220
tctggctgat gtacacttcc tgggtccttc cttcactcgc ctctgccctt tacactctgc      5280
ctgagaagcg tgtggctggg gaagtgggaa gcaagtatgg tctcttatgt gatcttggac      5340
tctgcaggtc tgaacccta ccccggcatc ctagtgaaca acaagttcta caactggtg      5400
aaggatggat accaaatggc ccagcctgta tttgcaccga agaacatgta cgcaaaggca      5460
ctcaacccag gggtgggtgg ttctagggtt ttggtagttg ttggaagagt gcatggccct      5520
ggtctctgtg tacaaggtgc tagagccagg tttccatctt cattgcattg aggttctcta      5580
cttagctttg aaccccagcg gcctcaagca tgctaacagg tgctgtatca ctgggccgta      5640
tctctagccc tcaaacttac ttttgactag tgctggggtc cttcacctct ccctggtgat      5700
ggatgtgccc gaggaggctg acacgggcaa cgcttgtctt gtttccagat acagcatcat      5760
gcagtcctgc tgggacctgg agcctaccag aagacccacc ttccaacaga tctgcttcct      5820
cctccaggag caggcccgac tggagaggag agaccaggtg agagggatgg agcagatgcc      5880
tggctggcta gagcaggctg ggccgggtct gggaaacttc agctgtttct ggcttctccc      5940
cacccagga ctatgctaac ctgccaagca gcggtggcag cagcggcagt gacagtggtg      6000
gtggcagcag cggtggcagc agcagtgagc cagaagagga gagctccagt gaacacctgg      6060
cctgctgtga gccaggggac atcgcccagc ccctgctgca gcctaacaac taccagttct      6120
gctgatcctc aggtgcaggc tgcctatcag aaggtggtgg ctggtgtggc caatgccctg      6180
gctcacaaat accactgaga tcttttttccc tctgccaaaa attatgggga catcatgaag      6240
ccccttgagc atctgacttc tggctaataa aggaaattta ttttcattgc aatagtgtgt      6300
tggaattttt tgtgtctctc actcggaagg acatatggga gggcaaatca tttaaaacat      6360
cagaatgagt atttggttta gagtttggca acatatgccc atatgctggc tgccatgaac      6420
aaaggttggc tataaagagg tcatcagtat atgaaacagc cccctgctgt ccattccatta      6480
ttccatagaa aagccttgac ttgaggttag attttttta tattttgttt tgtgttattt      6540
ttttcttta catccctaaa attttcctta catgttttac tagccagatt tttcctcctc      6600
tcctgactac tcccagtcat agctgtccct cttctcttat ggagatcgtt taaacaacg      6660
cggcacttaa gtagttaact ttaaataatg ccaattattt aaagttaata ggcgatcgca      6720
ccatatgaat ctcgaggtta tgtacctgac tgatgaagtt cctatacttt ctagagaata      6780
ggaacttcga agggttccgc aagctctagt cgagccccag ctggttcttt ccgcctcaga      6840
agccatagag cccaccgcat ccccagcatg cctgctattg tcttcccaat cctccccctt      6900
gctgtcctgc cccaccccac cccccagaat agaatgacac ctactcagac aatgcgatgc      6960
aatttcctca ttttattagg aaaggacagt gggagtggca ccttcaggg tcaaggaagg      7020
cacgggggag gggcaaacaa cagatggctg gcaactagaa ggcacagtcg aggctgatca      7080
gcgagctcta gagaattgat cccctcagaa gaactcgtca agaaggcgat agaaggcgat      7140
gcgctgcgaa tcgggagcgg cgataccgta aagcacgagg aagcggtcag cccattcgcc      7200
gccaagctct tcagcaatat cacgggtagc caacgctatg tcctgatagc ggtccgccac      7260
acccagccgg ccacagtcga tgaatccaga aaagcggcca ttttccacca tgatattcgg      7320
caagcaggca tcgccatggg tcacgacgag atcatcgccg tcgggcatgc gcgccttgag      7380
cctggcgaac agttcggctg gcgcgagccc ctgatgctct tcgtccagat catcctgatc      7440
gacaagaccg gcttccatcc gagtacgtgc tcgctcgatg cgatgtttcg cttggtggtc      7500
gaatgggcag gtagccggat caagcgtatg cagccgccgc attgcatcag ccatgatgga      7560
tactttctcg gcaggagcaa ggtgagatga caggagatcc tgccccggca cttcgcccaa      7620
tagcagccag tcccttcccg cttcagtgac aacgtcgagc acagctgcgc aaggaacgcc      7680
cgtcgtggcc agccacgata gccgcgctgc ctcgtcctga gttcattca gggcaccgga      7740
caggtcggtc ttgacaaaaa gaaccgggcg cccctgcgct gacagccgga acacggcggc      7800
atcagagcag ccgattgtct gttgtgccca gtcatagccg aatagcctct ccacccaagc      7860
ggccggagaa cctgcgtgca atccatcttg ttcaatggcc gatccatgg tttagttcct      7920
caccttgtcg tattatacta tgccgatata ctatgccgat gattaattgt caacaggctg      7980
caggtcgaaa ggcccggaga tgaggaagag gagaacagcg cggcagacgt gcgcttttga      8040
agcgtgcaga atgccgggcc tccggaggac cttcggggcg ccgccccgcc cctgagcccg      8100
ccccctgagcc cgccccgga cccacccctt cccagcctct gagcccagaa agcgaaggag      8160
caaagctgct attggccgct gccccaaagg cctacccgct tccattgctc agcggtgctg      8220
tccatctgca cgagactagt gagacgtgct acttccattt gtcacgtcct gcacgacgcg      8280
agctgcgggg cggggggaa cttcctgact aggggaggag tagaaggtgg cgcgaagggg      8340
```

-continued

```
ccaccaaaga acggagccgg ttggcgccta ccggtggatg tggaatgtgt gcgaggccag  8400
aggccacttg tgtagcgcca agtgcccagc ggggctgcta aagcgcatgc tccagactgc  8460
cttgggaaaa gcgcctcccc tacccggtag aatttcgacg acctgcagcc aaagcgctag  8520
agccagacat gataagatac attgatgagt ttggacaaac cacaactaga atgcagtgaa  8580
aaaaatgctt tatttgtgaa atttgtgatg ctattgcttt atttgtaacc attataagct  8640
gcaataaaca agtttagcta tccatcagtc gagaattggc tcccacggac actccgcccc  8700
ttctgagata ccgcatcagt gtttcaggct tcttccatgt cccttcctgc ataatctcga  8760
ccatagacac ctgtttctcg gccatgtcta ttgcggcacc caccctggcg gaatggccga  8820
tccaggtcct atacctccct ttattggggg tgggcgtcccg tttgttcagc agcacccagg  8880
catcactgaa aatcttctcc atggcagggg cggtcagggg cgtggtagta atgcgggctt  8940
tgtttgaccg gtgtataggt gggaagagca cagcgtctgg atgttctcta agcccactga  9000
cgtccagcca gtcattgagc actgctgtgg ttcgccggga gagcactttg tcaaggcccg  9060
cagctgtggt gattgtctta gtgtgactga tgtgcagggt cactgtgtct cctgtctgat  9120
ccaagtcccc aaccctgatg cgtgatattt cagacattct catgagggtg ttataggcta  9180
cgaacaggaa agccctgttg cgcaggtcga ccagccgctc gctcctgctg agcagcacat  9240
ccagcagctt caggtcgtcc cagcgcaggg ggattgcctg tcctgtcctc tcacccttt  9300
cggttgcggc ttctcttcta attcttctca tggcaagact cactgacttg tcgtcggaca  9360
agggtggcag tccgcagtgg gacagaagca tattaagcat agcatagtgc ttgtcgatgg  9420
tagtggaggc caggtctgca tcgtgcaact gaagaaagta ttcgcgtgcc atttcaggac  9480
taattggaaa ccatgcaagc tgccgagcat ggcaccatct ggcccagcta tgaaagacca  9540
acctcaaatc cctcaaagtg ttaggagcgt acgcccctg gtcattcata aacctcatga  9600
agtttcagc ggcctcctga tactcttttgc cgatgtttcg caggaatcca ccagatgaac  9660
cactaataat cagctcagaa accttcctct tcttcttagg catggccgca ggaaagcaga  9720
gccctgaagc tcccatcacc ggccaataag agccaagcct gcagtgtgac ctcatagagc  9780
aatgtgccag ccagcctgac cccaagggcc ctcaggcttg ggcacactgt ctctaggacc  9840
ctgagagaaa gacataccca tttctgctta gggccctgag gatgagccca ggggtggctt  9900
ggcactgaag caaaggacac tggggctcag ctggcagcaa agtgaccagg atgctggagc  9960
tttgacccag aagccagagg ccagaggcca ggacttctct tggtcccagt ccaccctcac  10020
tcagagcttt accaatgccc tctggatagt tgtcgggtaa cggtggacgc cactgattct  10080
ctggccagcc taggacttcg ccattccgct gattctgctc ttccagccac tggctgaccg  10140
gttggaagta ctccagcagt gccttggcat ccagggcatc tgagcctacc aggtccttca  10200
gtacctcctg ccagggcctg gagcagccag cctgcaacac ctgcctgcca agcagagtga  10260
ccactgtggg cacaggggac acagggtggg gcccacaaca gcaccattgt ccacttgtcc  10320
ctcactagta aaagaactct agggttgcgg ggggtggggg aggtctctgt gaggctggta  10380
agggatattt gcctggccca tggagctagc ttggctggac gtaaactcct cttcagacct  10440
gaagttccta tactttctag agaataggaa cttcggaatt cgatatcaag ctaagcttga  10500
ttaactttaa ataatgccaa ttatttaaag ttagtagcgt cgcacgtgaa atcgatataa  10560
cttcgtatag catacattat acgaagttat ggtaccggta acctatttgc aggaattgtt  10620
tagggtgtcta acgggttgtt gtgtatgcaa atgcttggaa ggcacctgg tattgtgtac  10680
ttggaggtgg cagctgttgg tgttgtgtat gaggtgggcc acaggctgct cacagcacag  10740
ggactcattg cctctgaggc aggagcagcc ctgtggctcc aagggccaga gggccattgg  10800
aaacagggct gtgggctag aattctaaat gttaaattgt ccacatcaaa tcgtctcaga  10860
cctcaggcct gcacaggttt agacaggagt agacagtaga ctaccaaaac ctgcatctac  10920
ttcaacagag acccaagacc tcctgctcct cctctggtcc tcaggcctca gggaaggata  10980
aactgactaa taatctctct gcgctttctt cagtgcatcc accgggacgt agcagctcga  11040
aacgtgctgt tgaccagcgg acatgtggcc aagattgggg actttggact ggctagggac  11100
atcatgaatg actccaacta tgttgtcaag ggcaatggta gtgccgagag agagagagag  11160
agagggaggg agagagagag agagagagag agagagagag agagagagag agagagagag  11220
agagagagag agagagattg agattggttg ggcaggctgt ggagagccct tgactgacat  11280
ggtactgtct tgtcaggccc gcctgcctgt aaagtggatg gccccagaga gcatctttga  11340
ctgcgtctac acagttcaga gtgatgtgtg gtcctacggc atcctcctct gggagatctt  11400
ctcgcttggt gagctgctaa gcctgttttc aggtgcagcc tagggctgac ccgtctttgg  11460
ctatgccatc ggtgtcttga acctcatgga cgaaatctac tcaaagatgt cggtgtccaa  11520
gacagagcaa gggctggcag gagcaatggg atggtgaggg ctcttgaacc agtactgcag  11580
cacctgtgtg taattcagac cctctggctg atgtacactt cctgggtcct tccttcactc  11640
gcctctgccc tttacactct gcctgagaag cgtgtggctg gggaagtggg aagcaagtat  11700
ggtctcttat gtgatcttgg actctgcagg tctgaacacc taccccggca tcctagtgaa  11760
caacaagttc tacaaactgg tgaaggatgg ataccaaatg gcccagcctg tatttgcacc  11820
gaagaacatg tacgcaaagg cactcaaccc aggggtgggt ggttcataggg ttttggtagt  11880
tgttggaaga gtgcatgggc ctggtctctg tgtacaaggt gctagagcca ggtttccatc  11940
ttcattgcat tgaggttctc tacttagctt tgaaccccag cggcctcaag catgctaaca  12000
ggtgctgtat cactgggccg tatctctagc cctcaaactt acttttgact agtgctgggg  12060
tccttcacct ctccctggtg atggatgtgc ccgaggaggc tgacacgggc aacgcttgtc  12120
ttgtttccag atacagcatc atgcagtcct gctgggacct ggagcctacc agaagaccca  12180
ccttccaaca gatctgcttc ctcctccagg agcaggcccg actggagagg agagaccagg  12240
tgagagggat ggagcagatg cctggctggc tagagcaggc tgggccgggt ctgggaaact  12300
tcagctgttt ctggcttctc cccacccagg gactatgcta acctgccaag cagcggtggc  12360
agcagcggca gtgacagtgg tggtggcagc agcggtggca gcagcagtga gccagaagag  12420
gagagctcca gtgaacacct ggcctgctgt gagcaggggg acatcgccca gccctgctg  12480
cagcctaaca actaccagtt ctgctgaagt gggagggaga gccgagtcct gccgctctct  12540
acgtcccagc ttggcctcct ccatggcacg ggcgacatgg ggagaacata tggacttcgc  12600
cctcagcttg gcccagctct gacacttcag aacatgaggg gtctgggag gtcagaggcc  12660
ccgtttgttc ccagagcctg ggccatcact gccagtgggg ttctcacagt gctagcctct  12720
atatttacta tgccaactgg tgcacccta gttctctttc ttccatcctat tcccatttta  12780
aaaaaacccgt cccaaactct cgtgtttcaa tggaaagact gatttatgtc tcaaaagaca  12840
agagtctcaa aggctgtggg taagctgaag gcttgcctcc ctgacagatg cttagactac  12900
aggcttcttg ggacaggtgg cccccttccta agctcacagg agtggccacc actcttgacc  12960
ttcactctgt ctatagtccc gcctcatcct ggatcttgta ctgagcggca gctaaaagtg  13020
ttctacccag tgccctgtca ctctagactg gaaggtatgg ggcctgatgc aaggctgacc  13080
```

-continued

```
acaccaacaa acaccgtgtg ctcctctcca agctgactcg tcctcattaa ctgtcaacat  13140
taaactaaca gcattaacac agccagcagg gtctggttct ttgcagcaca caggtgcctt  13200
caagctccct aggaccgacc tccttccacc tattcctcct gacaagggac caacaagcac  13260
ccacttccag agccaaggga cacagcattg aacaggctct tgcttcatca aaaccagata  13320
atttaataaa ctttattctt gttggggaa gaacgagagg gaaagccacc tatcccaccc  13380
tctcaataaa ttaaatagca cttggccaat cctgggccct aagcaaaccg cgggcacctg  13440
agcccatgct gctgtttgct tatggcccta tctgcttccc cttcacagaa gggagttttc  13500
ctactgcttg tcagctatgt cacaaccacg ggccacatcc cctctgtggt gagggtctga  13560
ggacccagag gacgtagggt atagtagcag tggccagaga aggaggaag gattctcttc  13620
ccccaaaccc ggggctgaga gagtcctgga ggagctgttc cttctcctca actgccccaa  13680
ggtgtgggaa cagggagagt tggaggaaca gagaatgcac ccctcctta gggagaatga  13740
agggccccaa gggattccaa gagtaaataa gccagcaagg caggctagga agcccacaag  13800
acaggagcca gagctcctcc ccgcgggaca gcttagctca atggcggctc cacctggtgc  13860
aggaacccgg gtggttgtgg gtctgggcaa ccaggccccg gccttcctat cagcaccaga  13920
tccttaagaa catcatgtcc tgcctccacg tgctctctca ggtcaaggag aggcttccca  13980
gcgcctctcc tgagccccag aggtcgaggc cccactgtgc tcatgaaatg gaagctcttt  14040
ggtcagttca agcagtcaga ggccctccct aaagaggact gcaggtccct caataggact  14100
gccctgggca agggccagat tatggcttga gagagatgat gcaggccctg tacataaaaa  14160
cctggcttat tccaccactg aggctacttc ctcttcctct ccttcctcct gggcctccgt  14220
cttgatctgg gcaaccccaa ggcgatagag ggtgtcgcga atgaccacct cgccaggctg  14280
gcagctctgc acaatgtcat ggatctgcct gttgacaatc tctcggctgg tgaggaagtc  14340
catgaggcgg ttgtagaggt aatagtgggt ggcattgtca aaggcgatgg gcctctggcg  14400
gacactgctg agcttgctgt ccgtggtaga ggcataaggt gccagctctg ggcacagtga  14460
taaggaacgg tggccagcac tggggtcact gggatcgggc tttgtgtttg catggacaat  14520
acgccgtgtc gcactcttgg tgactggatg ctgcactgag ttttcagcct ctgtcacatc  14580
cacagaataa tgctggtcca agagttcagg gcaggacaca ctctacaaga gagaagagaa  14640
gctgctctgt aagagggatg actgagggag aaccttgctg gagagagcag aagccaggca  14700
gccccgttta aatcctaaag gctgtgtaca ctgtgtctcc tgtgccccat ttcttcatgt  14760
aagaatgggc ataggaaaat ggtccccca gcacaggtgc tggactgttt gagagctata  14820
ccatcactgt acctggacaa tgtgggcacc agaggaatag gaggatctgg ctcggtggga  14880
cacttcagac acttttgggt gcggccgcgt accagctttt gttccctta gtgagggtta  14940
atttcgagct tggcgtaatc atggtcatag ctgtttcctg tgtgaaattg ttatccgctc  15000
acaattccac acaacatacg agccggaagc ataaagtgta aagcctgggg tgcctaatga  15060
gtgagctaac tcacattaat tgcgttgcgc tcactgcccg ctttccagtc gggaaacctg  15120
tcgtgccagc tgcattaatg aatcggccaa cgcgcgggga gaggcggttt gcgtattggg  15180
cgctcttccg cttcctcgct cactgactcg ctgcgctcgg tcgttcggct gcggcgagcg  15240
gtatcagctc actcaaaggc ggtaatacgg ttatccacag aatcagggga taacgcagga  15300
aagaacatgt gagcaaaagg ccagcaaaag gccaggaacc gtaaaaaggc cgcgttgctg  15360
gcgtttttcc ataggctccg cccccctgac gagcatcaca aaatcgacgc tcaagtcag  15420
aggtggcgaa acccgacagg actataaaga taccaggcgt ttccccctgg aagctccctc  15480
gtgcgctctc ctgttccgac cctgccgctt accggatacc tgtccgcctt tctcccttcg  15540
ggaagcgtgg cgctttctca tagctcacgc tgtaggtatc tcagttcggt gtaggtcgtt  15600
cgctccaagc tgggctgtgt gcacgaaccc ccgttcagcc cgaccgctgc gccttatcc  15660
ggtaactatc gtcttgagtc caacccggta agacacgact tatcgccact ggcagcagcc  15720
actggtaaca ggattagcag agcgaggtat gtaggcggtg ctacagagtt cttgaagtgg  15780
tggcctaact acggctacac tagaagaaca gtatttggta tctgcgctct gctgaagcca  15840
gttaccttcg gaaaaagagt tggtagctct tgatccggca aacaaaccac cgctggtagc  15900
ggtggttttt ttgtttgcaa gcagcagatt acgcgcagaa aaaaaggatc tcaagaagat  15960
cctttgatct tttctacggg gtctgacgct cagtggaacg aaaactcacg ttaagggatt  16020
ttggtcatga gattatcaaa aaggatcttc acctagatcc ttttaaatta aaaatgaagt  16080
tttaaatcaa tctaaagtat atatgagtaa acttggtctg acagttacca atgcttaatc  16140
agtgaggcac ctatctcagc gatctgtcta tttcgttcat ccatagttgc ctgactcccc  16200
gtcgtgtaga taactacgat acgggagggc ttaccatctg gccccagtgc tgcaatgata  16260
ccgcgagacc cacgctcacc ggctccagat ttatcagcaa taaaccagcc agccggaagg  16320
gccgagcga gaagtggtcc tgcaacttta tccgcctcca tccagtctat taattgttgc  16380
cgggaagcta gagtaagtag ttcgccagtt aatagtttgc gcaacgttgt tgccattgct  16440
acaggcatcg tggtgtcacg ctcgtcgttt ggtatggctt cattcagctc cggttcccaa  16500
cgatcaaggc gagttacatg atcccccatg ttgtgcaaaa aagcggttag ctccttcggt  16560
cctccgatcg ttgtcagaag taagttggcc gcagtgttat cactcatggt tatggcagca  16620
ctgcataatt ctcttactgt catgccatcc gtaagatgct tttctgtgac tggtgagtac  16680
tcaaccaagt cattctgaga atagtgtatg cggcgaccga gttgctcttg cccggcgtca  16740
atacgggata ataccgcgcc acatagcaga actttaaaag tgctcatcat ggaaaacgt  16800
tcttcggggc gaaaactctc aaggatctta ccgctgttga tccagttc gatgtaaccc  16860
actcgtgcac ccaactgatc ttcagcatct tttactttca ccagcgtttc tgggtgagca  16920
aaaacaggaa ggcaaaatgc cgcaaaaaag ggaataaggg cgacacggaa atgttgaata  16980
ctcatactct tcctttttca atattattga agcatttatc agggttattg tctcatgagc  17040
ggatacatat ttgaatgtat ttagaaaaat aaacaaatag gggttccgcg cacatttccc  17100
cgaaaagtgc cacctgacgc gccctgtagc ggcgcattaa gcgcggcggg tgtggtggtt  17160
acgcgcagcg tgaccgctac acttgccagc gccctagcgc cgcttccttt cgctttcttc  17220
ccttccttc tcgccacgtt cgccggcttt ccccgtcaag ctctaaatcg ggggctccct  17280
ttagggttcc gatttagtgc tttacggcac ctcgacccca aaaaacttga ttagggtgat  17340
ggttcacgta gtgggccatc gccctgatag acggtttttc gccctttgac gttggagtcc  17400
acgttcttta atagtggact cttgttccaa actggaacaa cactcaaccc tatctcggtc  17460
tattcttttg atttataagg gattttgccg atttcggcct attggttaaa aaatgagctg  17520
atttaacaaa aatttaacgc gaattttaac aaaatattaa                        17560
```

```
SEQ ID NO: 6          moltype = DNA   length = 23
FEATURE               Location/Qualifiers
source                1..23
```

-continued

```
                           mol_type = other DNA
                           organism = synthetic construct
SEQUENCE: 6
ggctggtaag ggatatttgc ctg                                                   23

SEQ ID NO: 7             moltype = DNA   length = 25
FEATURE                  Location/Qualifiers
source                   1..25
                         mol_type = other DNA
                         organism = synthetic construct
SEQUENCE: 7
tcatgctcca agaaattgtg gtaga                                                 25

SEQ ID NO: 8             moltype = DNA   length = 25
FEATURE                  Location/Qualifiers
source                   1..25
                         mol_type = other DNA
                         organism = synthetic construct
SEQUENCE: 8
gctgcttctc ctcataaaac atagt                                                 25

SEQ ID NO: 9             moltype = DNA   length = 25
FEATURE                  Location/Qualifiers
source                   1..25
                         mol_type = other DNA
                         organism = synthetic construct
SEQUENCE: 9
atttgcatac acaacaaccc gttag                                                 25

SEQ ID NO: 10            moltype = DNA   length = 22
FEATURE                  Location/Qualifiers
source                   1..22
                         mol_type = other DNA
                         organism = synthetic construct
SEQUENCE: 10
cttggctgga cgtaaactcc tc                                                    22

SEQ ID NO: 11            moltype = DNA   length = 24
FEATURE                  Location/Qualifiers
source                   1..24
                         mol_type = other DNA
                         organism = synthetic construct
SEQUENCE: 11
aagtacacaa taccaggtgc tttc                                                  24

SEQ ID NO: 12            moltype = DNA   length = 20
FEATURE                  Location/Qualifiers
source                   1..20
                         mol_type = other DNA
                         organism = synthetic construct
SEQUENCE: 12
aaggcgatag aaggcgatgc                                                       20

SEQ ID NO: 13            moltype = DNA   length = 20
FEATURE                  Location/Qualifiers
source                   1..20
                         mol_type = other DNA
                         organism = synthetic construct
SEQUENCE: 13
tcatctcacc ttgctcctgc                                                       20
```